US012564637B2

(12) United States Patent (10) Patent No.: US 12,564,637 B2
Tanner et al. (45) Date of Patent: Mar. 3, 2026

(54) NUCLEIC ACID MAZZOCCHIO AND METHODS OF MAKING AND USE THEREOF

(71) Applicant: The University of Hong Kong, Hong Kong (CN)

(72) Inventors: Julian Alexander Tanner, Hong Kong (CN); Simon Chi-Chin Shiu, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 1119 days.

(21) Appl. No.: 17/602,530

(22) PCT Filed: Apr. 9, 2020

(86) PCT No.: PCT/CN2020/083868
§ 371 (c)(1),
(2) Date: Oct. 8, 2021

(87) PCT Pub. No.: WO2020/207420
PCT Pub. Date: Oct. 15, 2020

(65) Prior Publication Data
US 2022/0168429 A1 Jun. 2, 2022

Related U.S. Application Data

(60) Provisional application No. 62/832,646, filed on Apr. 11, 2019.

(51) Int. Cl.
| | |
|---|---|
| A61K 47/00 | (2006.01) |
| A61K 47/54 | (2017.01) |
| A61K 47/69 | (2017.01) |
| A61K 49/00 | (2006.01) |
| B82Y 5/00 | (2011.01) |
| C12N 15/115 | (2010.01) |
| B82Y 40/00 | (2011.01) |

(52) U.S. Cl.
CPC ........ *A61K 47/549* (2017.08); *A61K 47/6929* (2017.08); *A61K 49/0002* (2013.01); *C12N 15/115* (2013.01); *B82Y 5/00* (2013.01); *B82Y 40/00* (2013.01); *C12N 2310/151* (2013.01); *C12N 2310/16* (2013.01); *C12N 2310/51* (2013.01); *C12N 2310/532* (2013.01)

(58) Field of Classification Search
CPC .................................. A61K 47/00; B82Y 5/00
See application file for complete search history.

(56) References Cited

U.S. PATENT DOCUMENTS

| | | | |
|---|---|---|---|
| 3,610,795 | A | 10/1971 | Antoine |
| 4,816,567 | A | 3/1989 | Cabilly |
| 5,487,994 | A | 1/1996 | Chandrasegaran |
| 5,521,063 | A | 5/1996 | Summerton |
| 5,624,821 | A | 4/1997 | Winter |
| 5,698,685 | A | 12/1997 | Summerton |
| 6,194,551 | B1 | 2/2001 | Idusogie |
| 6,453,242 | B1 | 9/2002 | Eisenberg |
| 2007/0111251 | A1 | 5/2007 | Rosania |
| 2007/0111270 | A1 | 5/2007 | Zhang |
| 2007/0117109 | A1 | 5/2007 | Rothemund |
| 2007/0154989 | A1 | 7/2007 | Barbas, III |
| 2007/0157328 | A1 | 7/2007 | Ramrakha |
| 2007/0287680 | A1 | 12/2007 | Cuchelkar |
| 2008/0311136 | A1 | 12/2008 | Beusker |
| 2009/0031733 | A1 | 2/2009 | Weaver, Jr. |
| 2009/0176660 | A1 | 7/2009 | Yla-Herttuala |
| 2009/0258926 | A1 | 10/2009 | Divita |
| 2009/0305329 | A1 | 12/2009 | Laszlo |
| 2010/0099627 | A1 | 4/2010 | Seger |

(Continued)

FOREIGN PATENT DOCUMENTS

| | | |
|---|---|---|
| CN | 107397960 A | 11/2017 |
| CN | 107430984 | 12/2017 |

(Continued)

OTHER PUBLICATIONS

Pan et al. (2017) "Structure and conformational dynamics of scaffolded DNA origami nanoparticles" Nucleic acids research, 45(11), 6284-6298. (Year: 2017).*

(Continued)

*Primary Examiner* — James Joseph Graber

(74) *Attorney, Agent, or Firm* — Pabst Patent Group LLP

(57) ABSTRACT

Provided herein are compositions and methods involving nucleic acid nanostructures that can encapsulate cargo for use in, for example, therapeutic, diagnostic, and analytical applications. The nanostructures can have a plurality of interconnected subunits configured such that the nanostructures have a continuous torus-like structure with a closed three-dimensional cavity. Preferably, the nanostructure is a nucleic acid mazzocchio. The subunits are connected by linkers having defined lengths to constrain the nanostructure into the continuous torus-like shape. The closed three-dimensional cavity is of defined size to encapsulate any cargo of interest. Cargo can also be positioned in the open hole at the center of the nanostructure. The cargo can be a wide range of compounds including, for example, chemical drugs, small molecules, therapeutics, targeting agents, enzymes, dyes, and fluorescent molecules. As such, the disclosed nanostructures are suitable for delivery of one or more therapeutic, toxic, imaging, diagnostic, or prophylactic agents.

19 Claims, 3 Drawing Sheets
Specification includes a Sequence Listing.

(56)     References Cited

U.S. PATENT DOCUMENTS

| 2016/0215317 A1 | 7/2016 | He |
| 2018/0016569 A1 | 1/2018 | Fu |

FOREIGN PATENT DOCUMENTS

| CN | 109196103 | 1/2019 | |
| WO | 2003016496 | 2/2003 | |
| WO | 2012061719 | 5/2012 | |
| WO | 2014018423 | 1/2014 | |
| WO | WO2017189870 A1 * | 11/2017 | ............ C12N 15/10 |
| WO | 2018007327 | 1/2018 | |
| WO | 2018017806 | 1/2018 | |
| WO | 2018031954 | 2/2018 | |
| WO | 2018165465 | 9/2018 | |

OTHER PUBLICATIONS

Veneziano et al. (2016) "Designer nanoscale DNA assemblies programmed from the top down" Science, 352(6293), 1534-1534. (Year: 2016).*

Arnida, et al., "Cellular uptake and toxicity of gold nanoparticles in prostate cancer cells: a comparative study of rods and spheres", J. Appl. Toxicol., 30(3):212-7 (2020).

Braasch, et al., "Locked nucleic acid (LNA): fine-tuning the recognition of DNA and RNA", Chem. Biol., 8(1):1-7 (2001).

Chithrani, et al., "Determining the size and shape dependence of gold nanoparticle uptake into mammalian cells", Nano. Lett., 6(4):662-8 (2006).

Cong, et al., "Multiplex Genome Engineering Using CRISPR/Cas Systems", Science, 339(6121):819-823 (2013).

Douglas, et al., "A logic-gated nanorobot for targeted transport of molecular payloads", Science, 335(6060):831-4 (2012).

Douglas, et al., "Self-assembly of DNA into nanoscale three-dimensional shapes", Nature, 459(7245):414-418 (2009).

Friedman, et al., "The smart targeting of nanoparticles", Curr. Pharm. Des., 19(35):6315-29 (2013).

Goodman, et al., "The single-step synthesis of a DNA tetrahedron", Chem. Commun., 12:1372-3 (2004).

Han, et al., "DNA Origami with compl;ex curvatures in three dimensional space", 332(6027):342-346 (2011).

He, et al., "Hierarchical self-assembly of DNA into symmetric supramolecular polyhedra", Nature, 452(184):198-201 (2008).

Hollinger, et al., "'Diabodies': small bivalent and bispecific antibody fragments", PNAS, 90(14):6444-48 (1993).

Hong, et al., "DNA Origami: Scaffolds for Creating Higher Order Structures", Chem. Rev., 117(20):12584-12640 (2017).

Huang, et al., "Size-dependent localization and penetration of ultrasmall gold nanoparticles in cancer cells, multicellular spheroids, and tumors in vivo", ACS Nano., 6(5):4483-93 (2012).

Hughes, et al., "Synthetic DNA Synthesis and Assembly: Putting the Synthetic in Synthetic Biology", Cold Spring Harb. Perspect. Biol., 9(1):a023812 (2017).

International Search Report for PCT/CN2020/083868 dated Jun. 30, 2020.

Jiang, et al., "DNA origami as a carrier for circumvention of drug resistance", Journal of the American Chemical Society, 134(32): 13396-13403 (2012).

Jiang, et al., "Multiple-Armed Tetrahedral DNA Nanostructures for Tumor-Targeting, Dual-Modality in Vivo Imaging", ACS Appl. Mater. Interfaces, 8(7):4378-84 (2016).

Ke, et al., "Three-dimensional structures self-assembled from DNA bricks", Science, 338(611):1177-1183 (2012).

Kim, et al., "Chimeric restriction endonuclease", PNAS, 91(3):883-887 (1994).

Lee, et al., "Molecularly self-assembled nucleic acid nanoparticles for targeted in vivo siRNA delivery", Nat. Nanotechnol., 7(6):389-93 (2012).

Martin, et al., "Cancer gene therapy by thyroid hormone-mediated expression of toxin genes", Cancer Res., 60(12):3218-3224 (2000).

Nielsen, et al., "Sequence-Selective Recognition of DNA by Strand Displacement with a Thymine-Substituted Polyamide", Science, 254(5037):1497-1500 (1991).

Pan, et al., "Structure and conformational dynamics of scaffolded DNA origami nanoparticles", Nucleic Acids Research, 45(11):6284-6298 (2017).

Seeman, et al., "DNA nanotechnology", Nature Reviews Materials, 3(17068):1-23 (2017).

Wang, et al., "Design and operation of reconfigurable two-dimensional DNA molecular arrays", Nat. Protoc., 13(10):2312-2329 (2018).

Xu, et al., "A physical model for the size-dependent cellular uptake of nanoparticles modified with cationic surfactants", Int. J. Nanomedicine, 7:3547-54 (2012).

Yang, et al. "DNA nanostructures constructed with multi-stranded motifs", Nucleic Acids Research, 4(6):3606-3611 (2017).

Yu, et al., "Receptor-targeted nanocarriers for therapeutic delivery to cancer", Mal. Membr. Biol., 27(7):286-98 (2010).

Zhao, et al., "Organizing DNA origami tiles into larger structures using preformed scaffold frames", Nano Lett., 11(7):2997-3002 (2011).

* cited by examiner

NUCLEIC ACID MAZZOCCHIO AND METHODS OF MAKING AND USE THEREOF

CROSS-REFERENCE TO RELATED APPLICATIONS

This application is a National Phase application under 35 U.S.C. 371 of PCT/CN2020/083868, filed Apr. 9, 2020, and claims priority to U.S. Provisional Application No. 62/832, 646, filed Apr. 11, 2019, the disclosures of which are hereby incorporated herein by reference in their entirety.

FIELD OF THE INVENTION

The disclosed invention is generally in the field of nucleic acid nanostructures and specifically in the area of mazzocchio based nucleic acid nanostructures for the delivery of cargo for therapeutic, diagnostic, and analytical applications.

BACKGROUND OF THE INVENTION

DNA is widely known as the biological material for the storage and transmission of genetic information. However, the understanding of its molecular structure and properties has allowed for the development of an entirely new field of DNA nanotechnology that takes the DNA molecule out of its biological context, and uses its information to assemble structural motifs and to connect them together. DNA nanotechnology allows use of DNA as bricks to fabricate objects for biomedical applications including synthetic biology, diagnostics and therapeutics. DNA appeals to nanoscientists for a variety of reasons including, first, the fact that DNA is a natural nanoscale material; second, a large number of techniques for studying DNA are already available; and third, DNA's ability to carry information can be exploited in the self-assembly process.

DNA nanotechnology uses the fundamental Watson-Crick base pairing principle in double-stranded DNA to fabricate various objects from DNA bricks to DNA origamis for various purposes (Seeman, N C., et al., *Nature Reviews Materials,* 3, 17068 (2017)). The field started from ideas around using Holliday junctions to build frameworks to assist protein crystallization (Seeman, N C, *J. Theor. Biol.,* 99(2):237-47 (1982)) and has rapidly led to the development of DNA nanotechnology for biomedical applications such as drug delivery (Douglas, S M., et al, *Science,* 335(6060): 831-4 (2012)) and small interfering RNA (siRNA) delivery into cells and animals (Jiang, D., et al., *ACS Appl. Mater. Interfaces,* 8(7):4378-84 (2016); Lee, H., et al., *Nat. Nanotechnol.,* 7(6):389-93 (2012)).

There are two general approaches for the rational design of DNA nanostructures (Wang, D., et al., *Nat. Protoc.,* 13(10):2312-2329 (2018)). One method is to use a tile-based approach with a small number of oligonucleotides which base-pair with each other to create repeating modular units. The DNA tetrahedron is the classic simple DNA nanostructure which can be simply synthesized through annealing of four oligonucleotides as demonstrated by Goodman, R P, et al., *Chem. Commun. (Camb),* 12:1372-3 (2004). There have been challenges for the limited size of the DNA tetrahedron such that double-bundle DNA tetrahedrons have been developed. More complex DNA polyhedra have been developed through self-assembly including the dodecahedron and Buckyball (He, Y. et al., *Nature,* 452(184):198-201 (2008)). The second method is the origami approach where a long single-stranded phage DNA is folded into a particular shape through the introduction of typically hundreds of short staple strand oligonucleotides. The staple strands contain segments or regions of complementary sequences to the scaffold that bring sequences that are far apart in sequence space to nearby locations in Euclidian space. These interactions and geometries are stabilized by specific Watson-Crick base pairing in the presence of salt that uses immobile Holliday junctions to constrain neighboring duplexes physically in space.

These two approaches carry different sets of advantages and disadvantages. The tile-based approaches tend to result in simpler structures that can be limited in terms of scale and complexity particularly when integrated into dynamic units. The origami-based approaches can result in highly impressive and complex nanostructures such as in George Church's nanorobot delivery (Douglas, S M., et al, *Science,* 335 (6060):831-4 (2012)), yet the requirement of several hundred oligonucleotide staples may limit their real-world application in therapeutics or diagnostics. The synthesis using hundreds of single-stranded DNA is a major drawback inhibiting the commercialization and clinical approval of DNA origamis for delivery purposes (e.g., US20070117109A1, US20180016569A1, and WO2018165465A1). Furthermore, there are challenges for protected delivery of cargo with both approaches. Various studies have demonstrated that the optimal diameter of nanoparticle for entry past the cell membrane is about 50-100 nm (Arnida, et al., *J. Appl. Toxicol.,* 30(3):212-7 (2020); Chithrani, B D., et al., *Nano. Lett,* 6(4)662-8 (2006); Huang, K., et al., *ACS Nano.,* 6(5):4483-93 (2012); Xu, A., et al., *Int. J. Nanomedicine,* 7:3547-54 (2012)). Even for simple nanostructures (see for example, CN107397960A and WO2018017806A1), they are restricted to delivery of certain types of cargos such as siRNA and small molecules due to their inability to protect a wide range of molecules in the way that a DNA origami is capable.

Thus, there is a need in the art for nanostructures that couple the benefits of encapsulation by DNA origami and the simplicity of smaller DNA nanostructures for drug delivery.

Therefore, it is an object of the invention to provide nucleic acid nanostructures that are economical and/or practical for biomedical applications (e.g., clinical drug delivery).

It is also an object of the invention to provide nucleic acid nanostructures with improved stability and/or reduced intrinsic toxicity.

It is also an object of the invention to provide nucleic acid nanostructures of optimal size for intracellular and/or intratissue delivery.

It is a further object of the invention to provide compositions containing nucleic acid nanostructures that allow targeting and delivery of cargo and their methods of use in therapeutic, diagnostic, and analytical applications.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF SUMMARY OF THE INVENTION

Disclosed are compositions and methods involving nucleic acid nanostructures that can encapsulate cargo for use in therapeutic, diagnostic, and analytical applications. In some forms, the nanostructures can have a continuous torus-like shape. In some forms, the torus-like shape is a mazzocchio. In some forms, the nanostructures can be composed of multiple subunits each having a defined polygonal shape in which the subunits are connected by linkers to form a structure having the continuous torus-like shape. In some forms, the subunits and linkers in the nanostructure form an extended supramolecular corkscrew. In some forms, the nanostructures can have one or more three-dimensional cavities of defined size that encapsulate cargo. In some forms, the cargo can be a wide range of compounds including chemical drugs, therapeutics, targeting moieties, enzymes, dyes, and fluorescent molecules. In some forms, the nanostructures can be used for delivery of one or more therapeutic, toxic, imaging, diagnostic, or prophylactic agents.

In particular, disclosed are compositions that include a nucleic acid nanostructure containing a plurality of subunits, in which the nanostructure has a continuous torus-like structure with a closed three-dimensional cavity. Each of the subunits can contain a core domain and a connecting domain, in which the core domain can define a polygon having a plurality of edges that enclose an open area, where the edges and open area define a plane of the subunit. A first edge of each subunit can be coplanar with the first edges of the other subunits, and each of the subunits can be between and connected to two other of the subunits with the planes of the connected subunits facing each other to form a stack of subunits. The planes of the connected subunits can be substantially perpendicular to the plane of the first edges of the subunits and tilted relative to the subunits connected to a given subunit in the direction horizontal to the plane of the first edges of the subunits. The tilt between the planes of connected subunits can produce a curve in the stack of subunits such that the connected subunits form the continuous torus-like structure with a closed three-dimensional cavity defined by the open areas of the stacked subunits. The connecting domain of each subunit can contain one or more linkers and the connection between the subunits can be made by the linkers. Each linker can have a length configured to create the tilt between the planes of connected subunits such that the continuous torus-like structure of the nanostructure is produced. The subunits and linkers in the nanostructure can form an extended supramolecular corkscrew.

The polygon of each of the subunits can be of any shape. For example, in some forms, the polygon of each of the subunits can be a hexagon, an octagon, a pentagon, a heptagon, a quadrilateral, or a triangle. In some forms, the nanostructure can have an internal diameter, an external diameter, or both, of 50-100 nm, inclusive. In some forms, the nanostructure can contain 8-40 subunits, inclusive, preferably 16 or 32 subunits. In some forms, each subunit contains 6-20 single-stranded nucleic acid strands. In preferred forms, each subunit contains 12 single nucleic acid strands.

In some forms, the core domain of the subunits contains one scaffold nucleic acid strand and n−1 staple nucleic acid strands, where n is the number of sides in the polygons of the subunits. Each staple strand can include a central region flanked by a 3' overhang region, a 5' overhang region, or both, and the central region of each staple strand can bind to the scaffold strand to form a duplex region. In preferred forms, the central region of the staple strand is flanked by both the 3' overhang region and the 5' overhang region.

In particular forms, the polygon of each of the subunits can be a hexagon or an octagon. Preferably, the polygon of each of the subunits is a hexagon.

In a particular form, the core domain can contain one scaffold nucleic acid strand (strand 1) and five staple nucleic acid strands (strands 2-6), where each staple strand includes a central region flanked by a 3' overhang region, a 5' overhang region, or both, and where the central region of each staple strand binds to the scaffold strand to form a duplex region. Preferably, the central region of the staple strand is flanked by both the 3' overhang region and the 5' overhang region.

In some forms, each pair of duplex regions adjacent to each other is configured to form a dihedral angle in which each of the dihedral angles is approximately the angle of a vertex of the polygon. Preferably, the dihedral angle can be 120°.

In some forms, each overhang can be at about a 90° dihedral angle to the flanking duplex region. The 5' overhangs of the staple strands can each individually contain 8-16 nucleotides, inclusive, the 3' overhangs can each individually contain 8-16 nucleotides, inclusive, or both.

In some forms, a thymidine residue can be present between one or more of the duplex regions. In some forms, a thymidine residue can be present between each of the duplex regions. In some forms, each duplex region of the subunit can contain 20 base pairs and a thymidine residue can be present between one or more of the duplex regions. In some forms, each duplex region of the subunit can contain 20 base pairs and a thymidine residue can be present between each duplex region. Some or all of the thymidine residues present between the duplex regions can be unpaired. In some forms, an unpaired thymidine residue can be present between one or more of the duplex regions. In some forms, an unpaired thymidine residue can be present between each of the duplex regions. In some forms, each duplex region of the subunit can contain 20 base pairs and an unpaired thymidine residue can be present between one or more of the duplex regions. In some forms, each duplex region of the subunit can contain 20 base pairs and an unpaired thymidine residue can be present between each of the duplex regions. In some forms, an unpaired thymidine residue can be present on one or more strands of the core domain between the central region and one or both of the overhang regions. In some forms, an unpaired thymidine residue can be present on each strand of the core domain between the central region and one or both of the overhang regions.

In some forms, the connecting domain can contain n single-stranded nucleic acid linkers that are complementary to one or more overhang regions of the core domain. In a preferred form, the connecting domain can contain six single-stranded nucleic acid linkers (strands 7-12) that are complementary to one or more overhang regions of the core domain. In some forms, the degree of complementarity between one or more linkers of the connecting domain and overhang regions of the core domain is in the range of 16-32 base pairs, inclusive.

In the disclosed nanostructures, the nucleic acid, nucleic acid strands, and linkers can be DNA. In some forms, all of the strands and linkers are unique in sequence.

In some forms, the disclosed nanostructures can further contain a therapeutic, toxic, targeting, imaging, diagnostic or prophylactic agent, or combinations thereof. In some forms, the disclosed nanostructures can further contain an imaging agent including, but not limited to, a gold nanoparticle. In some forms, the disclosed nanostructures can further contain a targeting agent including, but not limited to, an aptamer. In some forms, the disclosed nanostructures can further contain a molecule such as DNA, RNA, PNA, protein, peptide, lipid, carbohydrate, a small-molecule, or a dye. In some forms, the agent or molecule can be covalently or non-covalently bound to the nanostructure. In some forms, the agent or molecule can be encapsulated within the nanostructure.

Also provided are methods of making and using the disclosed nanostructures. For example, disclosed is a method of making any of the disclosed nanostructures by applying a temperature transition to a mixture of the scaffold strands, staple strands, and the linkers that make up the nanostructure, such that the strands and linkers anneal. In some forms, the subunits and linkers in the nanostructure form an extended supramolecular corkscrew. In some forms, the strands and linkers are present at approximately equal molar concentrations. In some forms, the temperature transition can occur over a period of 16 hours. In some forms, the temperature transition can involve a change in temperature from 90° C. to 20° C. Further disclosed are methods of delivery of a therapeutic, toxic, imaging, diagnostic, prophylactic agent, or combinations thereof to a subject by administering to the subject any of the nanostructures provided herein.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1C is a schematic showing that each subunit is composed of 12 single-stranded DNA strands, with 6 strands forming the core domain (1 scaffold strand (black) and 5 staples strands (various greys)) and 6 linker strands forming the connecting domain (grey strands). Each turning point (grey dot) contains an unpaired (i.e., single-stranded) thymidine residue. The duplex regions, as well as the 5' overhang and/or 3' overhang of each strand are apparent. FIG. 1D is a picture showing how the 16 hexagonal subunits of FIG. 1C are assembled into the simplified nucleic acid mazzocchio nanostructure.

DETAILED DESCRIPTION OF THE INVENTION

Figure 1A:
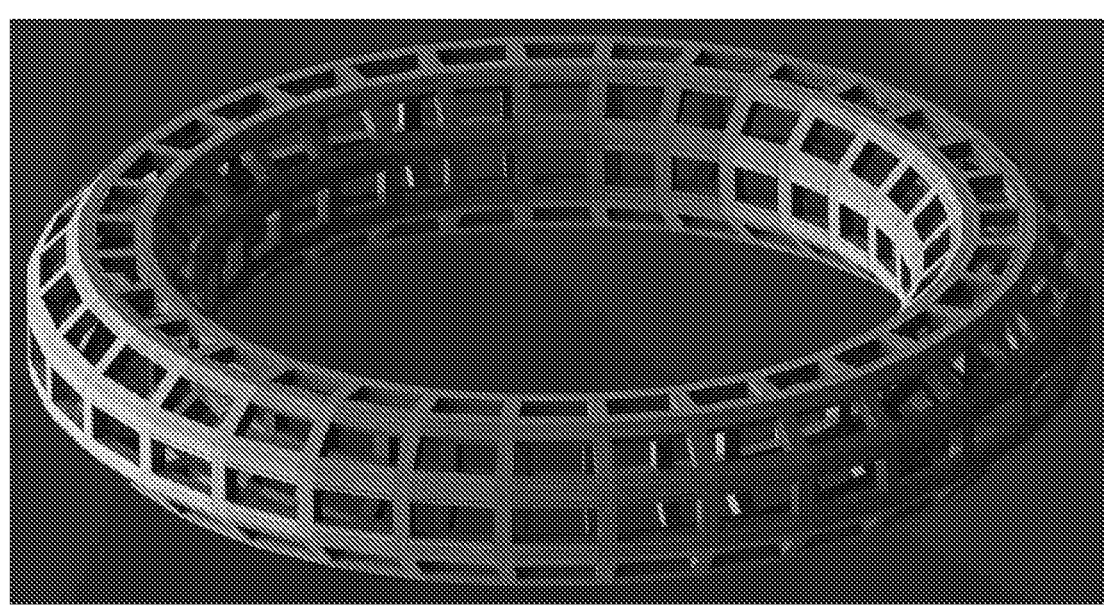
FIG. 1A is a diagram illustrating a mazzocchio originally depicted by Leonardo da Vinci. Da Vinci's mazzocchio is 32-subunit structure containing octagonal subunits.

The disclosed method and compositions can be understood more readily by reference to the following detailed description of particular embodiments and the Example included therein and to the Figures and their previous and following description.

It has been discovered that a nucleic acid nanostructure can be configured into a torus-like structure, such as a mazzocchio, for the encapsulation and/or presentation of cargo in applications such as therapeutic, diagnostic, and analytical applications. The disclosed nanostructure is a toroidal ring of polygons inspired by Da Vinci's 15th century investigations of geometry (Brecher, K. (2012). *The Mazzocchio in Perspective*. Paper presented at the Proceedings of Bridges 2012: Mathematics, Music, Art, Architecture, Culture). The mazzocchio has repeating tile subunits, each composed of a limited number of single-stranded oligonucleotides that assemble into an object of defined size and three-dimensional cavity. The size of the nanostructure can be configured by the length of each repeating unit and configured to contain a specific quantity of cargo. The cargo could be a wide range of molecules including but not limited to, biologics, chemical drugs, enzymes, and fluorescent molecules. The mazzocchio based nanostructure could be decorated with targeting molecules for cell surface epitopes such as aptamers to improve the specificity of delivery.

Compared to current nucleic acid nanostructure approaches, the disclosed mazzocchio based nanostructures are more cost effective to produce. For example, DNA origami nanostructures typically use hundreds of strands of single-stranded DNA, and hence costs can become an issue for real world, clinical applications. In contrast, the mazzocchio based nanostructures can typically use less than 20 oligonucleotides, and so are more practical and cost-effective, yet can still make complex three dimensional structures for the encapsulation of cargo.

Further, the disclosed mazzocchio based nanostructures have various advantages compared to previous drug delivery approaches in terms of ease of fabrication, stability and biocompatibility. For example, a mazzocchio based nanostructure could be made from just six to twelve single-stranded DNA sequences and can be customized for the size and quantity of cargos. The synthesis of the nanostructures is also a simple process. Typically, this involves mixing equal amounts of the single-stranded oligonucleotides, and heating and cooling without any sophisticated chemical reaction.

As shown in the Examples, a sixteen subunit, hexagonal, DNA mazzocchio nanostructure was successfully made having a diameter of about 50 to 60 nm. This size falls within the range known to be most effective for nanoparticles to penetrate cell membranes for drug delivery. The mazzocchio based nanostructures couple the benefits of encapsulation of a DNA origami to the simplicity of smaller DNA nanostructures for drug delivery. This immediately opens up a wide range of applications. Since the mazzocchio based nanostructure can have a cavity of defined dimension that is accessible yet still protected from the environment, the mazzocchio based nanostructures can encapsulate any cargo including, but not limited to, drugs, imaging reagents, analytical reagents, or diagnostic molecules (e.g., encapsulated during the assembly process) and can deliver them to a target cell or tissue. Other non-cellular biomedical applications are also contemplated.

Therefore, disclosed are compositions and methods involving nucleic acid nanostructures that can encapsulate cargo for use in therapeutic, diagnostic, and analytical applications. The nanostructures can have a continuous torus-like shape, such as a mazzocchio and can be composed of multiple subunits having a defined polygonal shape in which the subunits are connected by linkers to form the structure. The nanostructures can have one or more three-dimensional cavities of defined size that encapsulate cargo, including but not limited to, chemical drugs, therapeutics, targeting moieties, enzymes, dyes, and fluorescent molecules. The nanostructures can be used for delivery of one or more therapeutic, toxic, imaging, diagnostic, or prophylactic agents.

In particular, disclosed are compositions that include a nucleic acid nanostructure containing a plurality of subunits, in which the nanostructure has a continuous torus-like structure with a closed three-dimensional cavity. Each of the subunits can contain a core domain and a connecting domain, in which the core domain can define a polygon having a plurality of edges that enclose an open area, where the edges and open area define a plane of the subunit. A first edge of each subunit can be coplanar with the first edges of the other subunits, and each of the subunits can be between and connected to two other of the subunits with the planes of the connected subunits facing each other to form a stack of subunits. The planes of the connected subunits can be substantially perpendicular to the plane of the first edges of the subunits and tilted relative to the subunits connected to a given subunit in the direction horizontal to the plane of the first edges of the subunits. The tilt between the planes of connected subunits can produce a curve in the stack of subunits such that the connected subunits form the continuous torus-like structure with a closed three-dimensional cavity defined by the open areas of the stacked subunits. The connecting domain of each subunit can contain one or more linkers and the connection between the subunits can be made by the linkers. Each linker can have a length configured to create the tilt between the planes of connected subunits such that the continuous torus-like structure of the nanostructure is produced. The subunits and linkers in the nanostructure can form an extended supramolecular corkscrew.

The polygon of each of the subunits can be of any shape. For example, in some forms, the polygon of each of the subunits can be a hexagon, an octagon, a pentagon, a heptagon, a nonagon, a decagon, a quadrilateral (e.g., square, rectangle), or a triangle. In some forms, the nanostructure can have an internal diameter, an external diameter, or both, of 50-100 nm, inclusive. In some forms, the nanostructure can contain hundreds of subunits (e.g., about 100, about 200, about 300, about 400, about 500, or more). In some forms, it can be preferable to for the nanostructure to contain a smaller number subunits, such as less than 50 subunits. In preferred forms, the nanostructure can contain 8-40 subunits, inclusive, preferably 16 or 32 subunits. In some forms, each subunit contains 6-20 single-stranded nucleic acid strands. In preferred forms, each subunit contains 12 single nucleic acid strands.

In some forms, the core domain of the subunits contains one scaffold nucleic acid strand and n−1 staple nucleic acid strands, where n is the number of sides in the polygons of the subunits. Each staple strand can include a central region flanked by a 3' overhang region, a 5' overhang region, or both, and the central region of each staple strand can bind to the scaffold strand to form a duplex region. In preferred forms, the central region of the staple strand is flanked by both the 3' overhang region and the 5' overhang region.

In particular forms, the polygon of each of the subunits can be a hexagon or an octagon. Preferably, the polygon of each of the subunits is a hexagon.

In a particular form, the core domain can contain one scaffold nucleic acid strand (strand 1) and five staple nucleic acid strands (strands 2-6), where each staple strand includes a central region flanked by a 3' overhang region, a 5' overhang region, or both, and where the central region of each staple strand binds to the scaffold strand to form a duplex region. Preferably, the central region of the staple strand is flanked by both the 3' overhang region and the 5' overhang region. In some forms, each pair of duplex regions adjacent to each other is configured to form a dihedral angle in which each of the dihedral angles is approximately the angle of a vertex of the polygon. Preferably, the dihedral angle can be 120°.

In some forms, each overhang can be at about a 90° dihedral angle to the flanking duplex region. The 5' overhangs of the staple strands can each individually contain 8-16 nucleotides, inclusive, the 3' overhangs can each individually contain 8-16 nucleotides, inclusive, or both.

In some forms, a thymidine residue can be present between one or more of the duplex regions. In some forms, a thymidine residue can be present between each of the duplex regions. In some forms, each duplex region of the subunit can contain 20 base pairs and a thymidine residue can be present between one or more of the duplex regions. In some forms, each duplex region of the subunit can contain 20 base pairs and a thymidine residue can be present between each duplex region. Some or all of the thymidine residues present between the duplex regions can be unpaired (i.e., single-stranded). In some forms, an unpaired thymidine residue can be present between one or more of the duplex regions. In some forms, an unpaired thymidine residue can be present between each of the duplex regions. In some forms, each duplex region of the subunit can contain 20 base pairs and an unpaired thymidine residue can be present between one or more of the duplex regions. In some forms, each duplex region of the subunit can contain 20 base pairs and an unpaired thymidine residue can be present between each of the duplex regions. In some forms, an unpaired thymidine residue can be present on one or more strands of the core domain between the central region and one or both of the overhang regions. In some forms, an unpaired thymidine residue can be present on each strand of the core domain between the central region and one or both of the overhang regions.

Figure 1B:
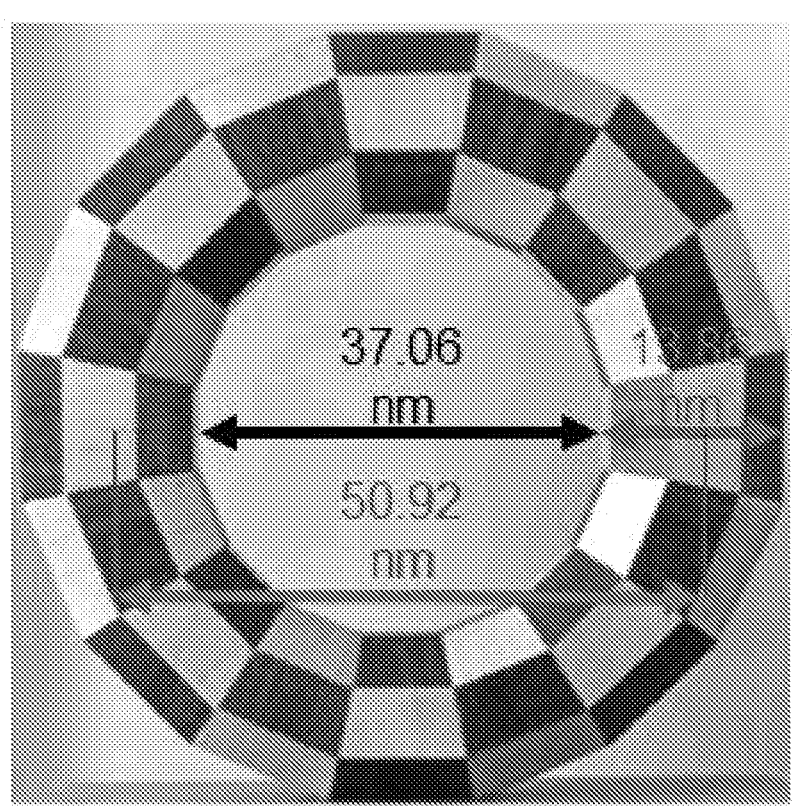
FIG. 1B is a schematic illustrating a simplified nucleic acid mazzocchio inspired by da Vinci's original, but containing 16 hexagonal subunits.
Figure 1C:
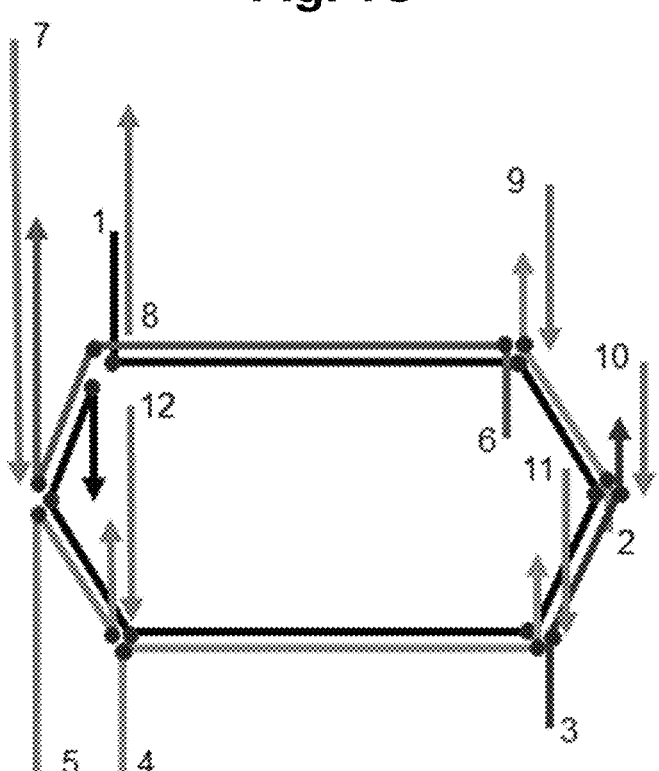
FIGS. 1C-1D illustrate the design of an exemplary DNA hexagonal subunit contained in the mazzocchio of FIG. 1B.
Figure 1D:
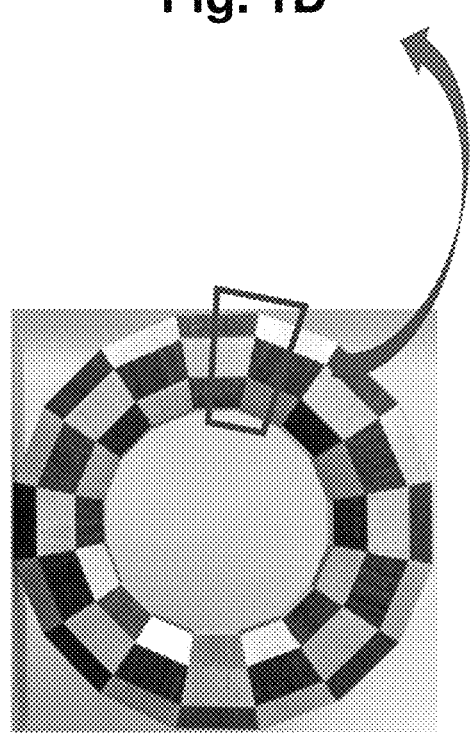

In some forms, the unpaired thymidine residue is positioned between one or more pairs of adjacent duplex regions (e.g., at the intersection of an overhang and duplex region; see FIG. 1C). The intersection of an overhang and duplex region can be referred to as the turning point of the subunit. In some forms, the unpaired thymidine residue is positioned between each pair of adjacent duplex regions (i.e., at each turning point). In some forms, the connecting domain can contain n single-stranded nucleic acid linkers that are complementary to one or more overhang regions of the core domain. In a preferred form, the connecting domain can contain six single-stranded nucleic acid linkers (strands 7-12) that are complementary to one or more overhang regions of the core domain. In some forms, the degree of complementarity between one or more linkers of the connecting domain and overhang regions of the core domain is in the range of 16-32 base pairs, inclusive.

In the disclosed nanostructures, the length of scaffold strand(s), staple strands and linker strands can vary depending on a number of variables including the desired shape and size of the nanostructure. For example, in some forms, the optimal diameter (e.g., internal diameter, an external diameter, or both) of a mazzocchio nanostructure is about 50-100 nm. In such forms, the length of the scaffold strand(s), staple strands and linker strands can be configured to be proportional to each other such that a mazzocchio nanostructure of this optimal diameter is attained. For example, the scaffold strand can include about 70-560 nucleotides, inclusive; the staple strands can include about 13-219 nucleotides, inclusive; and the linker strands can include about 2-58 nucleotides, inclusive.

In the disclosed nanostructures, the nucleic acid, nucleic acid strands, and linkers can be DNA. In some forms, all of the strands and linkers are unique in sequence.

In some forms, the disclosed nanostructures can further contain a therapeutic, toxic, targeting, imaging, diagnostic or prophylactic agent, or combinations thereof. In some forms, the disclosed nanostructures can further contain an imaging agent including, but not limited to, a gold nanoparticle. In some forms, the disclosed nanostructures can further contain a targeting agent including, but not limited to, an aptamer. In some forms, the disclosed nanostructures can further contain a molecule such as DNA, RNA, PNA, protein, peptide, lipid, carbohydrate, a small-molecule, or a dye. In some forms, the agent or molecule can be covalently or non-covalently bound to the nanostructure. In some forms, the agent or molecule can be encapsulated within the nanostructure.

Also provided are methods of making and using the disclosed nanostructures. For example, disclosed is a method of making any of the disclosed nanostructures by applying a temperature transition to a mixture of the scaffold strands, staple strands, and the linkers that make up the nanostructure, such that the strands and linkers anneal. In some forms, the subunits and linkers in the nanostructure form an extended supramolecular corkscrew. In some forms, the strands and linkers are present at approximately equal molar concentrations. In some forms, the temperature transition can occur over a period of 16 hours. In some forms, the temperature transition can involve a change in temperature from 90° C. to 20° C. Further disclosed are methods of delivery of a therapeutic, toxic, imaging, diagnostic, prophylactic agent, or combinations thereof to a subject by administering to the subject any of the nanostructures provided herein.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a nanostructure is disclosed and discussed and a number of modifications that can be made to a number of components including the nanostructure are discussed, each and every combination and permutation of nanostructure and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

The terms "nucleic acid molecule," "nucleic acid sequence," "nucleic acid fragment," "oligonucleotide," and "polynucleotide" are used interchangeably and are intended to include, but not limited to, a polymeric form of nucleotides that can have various lengths, either deoxyribonucleotides (DNA) or ribonucleotides (RNA), or analogs or modified nucleotides thereof, including, but not limited to locked nucleic acids (LNA), peptide nucleic acids (PNA), and morpholinos. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term can be applied to the polynucleotide molecule itself. This alphabetical representation can be input into databases in a computer having a central processing unit and used for bioinformatics applications such as functional genomics and homology searching. Oligonucleotides can optionally include one or more non-standard nucleotide(s), nucleotide analog(s) and/or modified nucleotides. In some cases nucleotide sequences are provided using character representations recommended by the International Union of Pure and Applied Chemistry (IUPAC) or a subset thereof. IUPAC nucleotide codes used herein include, A=Adenine, C=Cytosine, G=Guanine, T=Thymine, U=Uracil, R=A or G, Y=C or T, S=G or C, W=A or T, K=G or T, M=A or C, B=C or G or T, D=A or G or T, H=A or C or T, V=A or C or G, N=any base, "." or "-"=gap. In some forms the set of characters is (A, C, G, T, U) for adenosine, cytidine, guanosine, thymidine, and uridine respectively. In some forms the set of characters is (A, C, G, T, U, I, X, T, R, Y, N) for adenosine, cytidine, guanosine, thymidine, uridine, inosine, uridine, xanthosine, pseudouridine respectively.

The terms "nucleic acid nanostructure" or "nanostructure" are used interchangeably, and as used herein, refer to nucleic acid objects having desired shapes and sizes formed by assembly or polymerization of a plurality of polygonal subunits interconnected via linker strands. Each subunit can be formed using multiple short single strands of nucleic acids (staple strands) (e.g., DNA) to direct the folding of a longer, single strand of polynucleotide (scaffold strand) into desired shapes. Typically, in each subunit of the nanostructure, a single-stranded nucleic acid sequence is routed throughout the entire subunit. The nanostructure subunits optionally include oligonucleotide staple strands that hybridize to the scaffold sequence and create the polygonal structure. When the subunits do not include staple strands, the scaffold sequence hybridizes to itself to create the subunit having desired polygonal shape. Generally, the subunits and linkers in the nanostructure form an extended supramolecular corkscrew. It will be appreciated that where compositions, methods, and systems herein are exemplified with DNA (e.g., DNA mazzocchio), other nucleic acid molecules can be substituted. The nucleic acid nanostructure can be composed of deoxyribonucleotides (DNA) or ribonucleotides (RNA), or analogs or modified nucleotides thereof, including, but not limited to locked nucleic acids (LNA), peptide nucleic acids (PNA), and morpholinos.

The terms "scaffold strand," "scaffold sequence" or "scaffold nucleic acid strand" are used interchangeably and refer to a single strand of polynucleotide that is folded into desired shapes on the order of about 10 nm to a micron, or more. In some forms, scaffold sequences are folded into subunits of defined geometry by hybridization to small nucleic acid "staple strands." Alternatively, single-stranded nucleic acid scaffolds can be designed to fold without helper strands, for example, using parallel or paranemic crossover motifs. The scaffold strand can be composed of deoxyribonucleotides (DNA) or ribonucleotides (RNA), or analogs or modified nucleotides thereof, including, but not limited to locked nucleic acids (LNA), peptide nucleic acids (PNA), and morpholinos. The terms "staple strands," "staple nucleic acid strands" or "helper strands" are used interchangeably. "Staple strands" or "helper strands" refer to oligonucleotides that work as glue to hold the scaffold nucleic acid strand in its defined geometry and/or the nanostructure in its three-dimensional geometry. Additional nucleotides can be added to the staple strand at either 5' end or 3' end, and those are referred to as "staple overhangs".

"Overhang" and "overhang region" are used interchangeably and refer to the segment of an oligonucleotide that is not bound or not designed to bind another oligonucleotide. As such, overhangs are not limited to staple strands, and can be included with scaffold strands as well. An overhang at the 5' terminus is referred to as the "5' overhang region", while an overhang at the 3' terminus is referred to as the "3' overhang region." Overhangs can be functionalized to have desired properties such as a specific sequence to hybridize to a target nucleic acid sequence, or a targeting element. In some instances, the overhang can be biotinylated (e.g., for capturing the nanostructure on a streptavidin-coated bead). In some instances, the overhang can also be modified with chemical moieties. Non-limiting examples include Click-chemistry groups (e.g., azide group, alkyne group, DIBO/DBCO), amine groups, and thiol groups. In some instances, the overhang contains sequences designed to hybridize other nucleic acid sequences such as those on overhangs of other nucleic acid nanostructures. In other instances, the overhang contains one or more sites for conjugation to a molecule. For example, the overhang can be conjugated to a protein, or non-protein molecule, for example, to enable affinity-binding of the nucleic acid nanostructures. Exemplary proteins for conjugating to overhang tags include biotin and antibodies, or antigen-binding fragments of antibodies. In some instances, some bases located inside the oligonucleotide can be modified using base analogs (e.g., 2-Aminopurine, Locked nucleic acids, such as those modified with an extra bridge connecting the 2' oxygen and 4' carbon) to serve as linker to attach functional moieties (e.g., lipids, proteins). Alternatively, DNA-binding proteins or guide RNAs can be used to attach secondary molecules to the DNA scaffold.

"Degree of complementarity" as used herein, refers to the number of residues that are complementary between any two nucleic acid strands that are hybridized together.

"Continuous" as used in the context of structural configuration of a nanostructure refers to the characteristic of not having a defined start and/or end. That is, the nanostructure is a closed, unbroken or uninterrupted whole. This can be easily visualized in context of the disclosed DNA mazzocchio nanostructures, which are torus like, having a closed 3D ring (see FIGS. 1A-1B).

"Closed" as used herein in the context of the three dimensional cavity formed by the nanostructure refers to the absence of gaps, openings, or discontinuities in the regular spacings between the subunits and their components (e.g., core domain and connecting domain). It will be appreciated that the subunits and their connections leave open spaces between the subunits and their connections, as is also the case for the inspirational mazzocchio (FIG. 1A). Such open spaces are not gaps, openings, or discontinuities in the regular spacings between the subunits and their components because these are the regular spacings. Thus, it is the absence of additional gaps, openings, or discontinuities that makes the three dimensional space closed as defined herein.

"Polygonal diameter" as used herein refers to the diameter of the polygon defined by the core domain of subunit within a nanostructure. For example, this can be the diameter of the three-dimensional cavity defined by the open areas of the stacked subunits contained in the nanostructure. For example, see 13.86 nm line of FIG. 1B. Methods of determining the diameter of given polygon are known in the art.

"Torus-like structure" and "toroidal structure" as used herein in connection with the nanostructures refers to the shape of the nanostructure in which the nanostructure generally corresponds to a toroid shape. A toroid is a surface of revolution with a hole in the middle, like a doughnut, forming a solid body. The axis of revolution passes through the hole and so does not intersect the surface. For example, when a rectangle is rotated around an axis parallel to one of its edges, then a hollow rectangle-section ring is produced. As disclosed herein, the polygon formed by the subunits defines the cross section of the nanostructure and the revolved figure that forms the torus-like structure. The polygon (revolved figure) can be any of various polygons, such as hexagon, octagon, pentagon, heptagon, nonagon, decagon, quadrilateral (e.g., square, rectangle), triangle, etc. If the revolved figure is a circle, then the object is called a torus.

"Internal diameter" as used herein in connection with the nanostructures refers to the length of any straight line segment passing through the center of the hole in the middle of the torus-like structure (this hole is akin to the hole of a doughnut) and whose endpoints lie on the innermost edges of the central hole of the torus-like structure. For example, see 37.06 nm line of FIG. 1B.

"External diameter" as used herein in connection with the nanostructures refers to the length of any straight line segment passing through the center of the hole in middle of the torus-like structure (this hole is akin to the hole of a doughnut) and whose endpoints lie on the outermost edges/sides of the torus-like structure.

"Enclosed diameter" as used herein in connection with the nanostructures refers to the length of any straight line segment passing through the center of the hole in middle of the torus-like structure and whose endpoints lie in the center of the cavity on opposite sides of the torus-like structure. For example, see 50.92 nm line of FIG. 1B.

As used herein, the term "supramolecular corkscrew" refers a supramolecular helix that has a corkscrew character, such as the corkscrew character epitomized in a double helix formed of two nucleic acid strands. A supramolecular corkscrew is a form of supramolecular assembly in which multiple molecules assemble together to form a structure. Thus, a supramolecular corkscrew in the context of the disclosed nucleic acid nanostructures is an assembly of multiple nucleic acid molecules that hybridize in a corkscrew helix, with the subunits and linkers thus forming an extended supramolecular corkscrew. A preferred form of the corkscrew is represented by the double helix formed between linkers of connecting domains in individual subunits.

As used herein, the term "agent" is used broadly to mean a physical, chemical, or biological material that generally imparts a biologically useful function to a cargo being carried, presented, and/or delivered by a nanostructure. An agent can be any natural or non-natural material including, without limitation, a biological material, such as a cell, phage or other virus; an organic chemical such as a small molecule; a nanoparticle, a radionuclide; a nucleic acid molecule or oligonucleotide; a lipid; a saccharide or polysaccharide; a polypeptide; or a peptide. Agents can have any purpose, for example, without limitation, imaging or detection, therapeutic use, diagnostic use, toxic use, or combinations thereof. For example, agents can affect the target, such as agents with therapeutic effect, or can facilitate detection, visualization or imaging of the target, such as fluorescent molecule or radionuclides.

The terms "targeting agent" or "targeting molecule" refer to a substance which can direct a nanostructure to a receptor site on a selected cell or tissue type, can serve as an attachment molecule, or serve to couple or attach another molecule. The term "direct" refers to causing a molecule to preferentially attach to a selected cell or tissue type. This can be used to direct cellular materials, molecules, or drugs, as discussed below.

The term "small molecule," as used herein, generally refers to an organic molecule that is less than about 2,000 g/mol in molecular weight, less than about 1,500 g/mol, less than about 1,000 g/mol, less than about 800 g/mol, or less than about 500 g/mol. Small molecules are non-polymeric and/or non-oligomeric.

As used herein, the term "peptide" refers to a class of compounds composed of amino acids chemically bound together. In general, the amino acids are chemically bound together via amide linkages (CONH); however, the amino acids can be bound together by other chemical bonds known in the art. For example, the amino acids can be bound by amine linkages. Peptide as used herein includes oligomers of amino acids and small and large peptides, including polypeptides.

B. Compositions

1. Nucleic Acid Nanostructures

Disclosed are nucleic acid nanostructures optionally containing one or more cargo. Generally, the disclosed nucleic acid nanostructures are primarily assembled from and composed of nucleic acid molecules. Generally, the disclosed nucleic acid nanostructures are assembled, structured, and/or held together by nucleic acid hybridization. In some forms, the disclosed nucleic acid nanostructures are assembled, structured, and/or held together, at least in part, by pyrimidine dimers.

The nucleic acids forming the nanostructures can be any form of nucleic acid, including, for example, DNA, RNA mixtures of DNA and RNA, nucleic acids including or composed of modified nucleotides and/or modified nucleic acids, such as peptide nucleic acids (PNA). The nucleic acids can be single-stranded or double stranded, or contain portions of both double stranded or single-stranded sequence. The nucleic acid can be DNA (e.g., both genomic and cDNA), RNA, or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, and the like. Such nucleic acids comprise nucleotides and nucleoside and nucleotide analogs, and modified nucleosides such as amino modified nucleosides. In addition, "nucleoside" includes non-naturally occurring analogs. The composition of nucleic acid molecules used in the nucleic acid assemblies can be chosen as needed to confer specific properties/advantages, for example, stability, biocompatibility, encapsulation and/or release of cargo, and the like.

The disclosed nucleic acid nanostructures are structures of any arbitrary geometric shape. In preferred forms, the nucleic acid nanostructures can be of three-dimensional shapes. In some forms, the nucleic acid nanostructures have a torus-like shape. In some forms, the nucleic acid nanostructures have a mazzocchio shape.

It is known that nanoparticles smaller than 30 nm or larger than 200 nm tend to be cleared from the plasma circulation much more rapidly than nanoparticles with a size between 30 nm and 200 nm. As such, for applications involving administration of the disclosed nanostructures to a subject, it is preferred (although not required) that the nanostructures have a size (e.g., polygonal diameter, internal diameter, external diameter, enclosed diameter, or combinations) in this range (i.e., 30-200 nm, inclusive), preferably within 50-100 nm, inclusive. For example, the nanostructures can have a size of 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, and 200 nm, without limitation. The ordinary artisan will immediately recognize that all sizes within this range are contemplated, and that all of the sizes falling within the range are not specifically listed herein solely to conserve space. Further, it is understood that all ranges defined by all size points falling within this range are contemplated and that each range is not specifically listed herein solely to conserve space in this document and/or to avoid disclosure of what is immediately evident to the ordinary artisan.

i. Design and Manufacture

As discussed above, there are generally two approaches for making different types of nucleic acid nanostructures: (1) tile-based methods, and (2) scaffolded DNA origami. The tile-based approach typically uses a small number of oligo-nucleotides which base-pair with each other to create repeat-ing modular units. The origami approach typically involves folding a long single-stranded polynucleotide, referred to as a "scaffold strand," into a desired shape or structure using a number of small "staple strands" as glue to hold the scaffold in place. DNA origami is the nanoscale folding of DNA to create arbitrary two and three-dimensional shapes at the nanoscale. The specificity of the interactions between complementary base pairs make DNA a useful construction material, through design of its base sequences.

The disclosed methods and compositions utilize elements from both approaches. For example, disclosed are compo-sitions that include a nucleic acid nanostructure containing a plurality of subunits, in which the nanostructure has a continuous torus-like structure with a closed three-dimen-sional cavity (e.g., a mazzocchio based DNA nanostructure or DNA mazzocchio). Typically, the plurality of subunits contains a plurality of identical subunits akin to the repeat-ing modular units of the tile-based approach. Each of the subunits contains a core domain and a connecting domain. In some forms, the core domain can contain a scaffold nucleic acid strand and staple nucleic acid strands that hybridize to the scaffold strand to fold it into a particular pattern akin to the origami approach. The subunits and linkers in the nanostructure form an extended supramolecu-lar corkscrew.

Many designs and methods are known for making differ-ent types of nucleic acid nanostructures, such as DNA tile-based structures, and scaffolded DNA origami struc-tures. Many of these methods and designs can be used with and adapted to the disclosed nucleic acid nanostructures.

Exemplary methods include those described by Benson E et al (Benson E et al., Nature 523, 441-444 (2015)), Rothe-mund P W et al (Rothemund P W et al., Nature. 440, 297-302 (2006)), Douglas S M et al., (Douglas S M et al., Nature 459, 414-418 (2009)), Ke Y et al (Ke Y et al., Science 338: 1177 (2012)), Zhang F et al (Zhang F et al., Nat. Nanotechnol. 10, 779-784 (2015)), Dietz H et al (Dietz H et al., Science, 325, 725-730 (2009)), Liu et al (Liu et al., Angew. Chem. Int. Ed., 50, pp. 264-267 (2011)), Zhao et al (Zhao et al., Nano Lett., 11, pp. 2997-3002 (2011)), Woo et al (Woo et al., Nat. Chem. 3, pp. 620-627 (2011)), and Torring et al (Torring et al., Chem. Soc. Rev. 40, pp. 5636-5646 (2011)), which are incorporated here in the entirety by reference.

Exemplary methods for the top-down design of nucleic acid nanostructures of arbitrary geometry are described in Venziano et al, *Science,* 352 (6293), 2016, the contents of which are incorporated by reference in entirety.

In some forms, the sequence of the nanostructure is designed manually, or using alternative computational sequence design procedures. Exemplary design strategies that can be incorporated into the methods for making and using NMOs include single-stranded tile-based DNA ori-gami (Ke Y, et al., *Science* 2012); brick-like DNA origami, for example, including a single-stranded scaffold with helper strands (Rothemund, et al., and Douglas, et al.); and purely single-stranded DNA that folds onto itself in PX-origami, for example, using paranemic crossovers.

Alternative nanostructures include bricks, bricks with holes or cavities, assembled using DNA duplexes packed on square or honeycomb lattices (Douglas et al., *Nature* 459, 414-418 (2009); Ke Y et al., Science 338: 1177 (2012)). Paranemic-crossover (PX)-origami in which the nanostruc-ture is formed by folding a single long scaffold strand onto itself can alternatively be used, provided bait sequences are still included in a site-specific manner.

When scaffolded nucleic acid origami is used for the design and making of the disclosed nanostructures and/or subunits thereof, this generally involves building a geomet-ric model of a nucleic acid structure that will approximate the desired shape/geometry. The shape is filled from top to bottom by an even number of parallel double helices, idealized as cylinders. The helices are cut to fit the shape in sequential pairs and are constrained to be an integer number of turns in length. To hold the helices together, a periodic array of crossovers is incorporated; these crossovers desig-nate positions at which strands running along one helix switch to an adjacent helix and continue there. The resulting model approximates the shape within one turn (such as 3.6 nm) in the x-direction and roughly two helical widths (such as 4 nm) in the y-direction. DNA lattice parallel helices in such structures are not close-packed, perhaps owing to electrostatic repulsion. Thus, the exact y-resolution depends on the gap between helices. The gap, in turn, appears to depend on the spacing of crossovers.

In DNA origami, the basic technique for creating shapes involves folding a long single-stranded polynucleotide, referred to herein as a "scaffold strand", into a desired shape or structure using a number of small "helper strands" as glue to hold the scaffold in place. The number of helper strands will depend upon the size of the scaffold strand and the complexity of the shape or structure. For example, for relatively short scaffold strands (e.g., about 150 to 1500 base in length) and/or simple structures, the number of helper strands can be small (e.g., about 4 to 40, such as 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40). For longer scaffold strands (e.g., greater than 1500 bases) and/or more complex structures, the number of helper strands can be several hundred to thousands. In some examples, the number of helper strands can be about 300 to 600, including 300, 400, 500 or 600. In some forms, each staple/helper strand can have a length of about 20 to 60 base pairs, such as 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 base pairs.

The disclosure provides methods for creating any desired shape or structure out of a polynucleotide. Once the shape or structure has been created, any desired pattern or ligand can be added to the shape or structure. For example, a triangular structure can be created. In another example, a rectangle can be made. In some examples, the resolution of the shapes or structures is about 6 nanometers in one direction and about 3 nanometers in the other. For example, with internal labels on helper/staple strands the resolution can be reduced to about 3 nm. It is contemplated that this disclosure covers additional shapes or geometries recognized as suitable by those of ordinary skill upon studying the present disclosure. After the desired structure has been generated, additional patterns, materials or structures can be added.

Several factors contribute to the success of scaffold nucleic acid origami for application to design and manufacture of the disclosure. These include, but are not limited to (1) strand invasion, (2) an excess of staples, (3) cooperative effects and (4) design that intentionally does not rely on binding between staples. Briefly, strand invasion allows correct binding of excess full-length staples to displace unwanted secondary structure, incorrect staples, or grossly truncated staples. Further, each correct addition of a staple organizes the scaffold for subsequent binding of adjacent staples and precludes a large set of undesired secondary structures. Last, because staples are not designed to bind one another, their relative concentrations do not matter.

Also disclosed are methods of assembly of the scaffold strands, staple strands, and linker strands into the corresponding nucleic acid nanostructure having the desired shape and size. In some forms, assembly is in part, carried out by hybridization of the staples strands to the scaffold sequence. In some forms, the core domains of the subunits of the nucleic acid nanostructure include only single-stranded DNA oligonucleotides. In some forms, the core domains of the subunits of the nucleic acid nanostructure include a single-stranded DNA molecule folded onto itself. Therefore, in some forms, the nanostructures are assembled by DNA origami annealing reactions. Generally, the subunits and linkers in the nanostructure form an extended supramolecular corkscrew.

Typically, annealing can be carried out according to the specific parameters of the staple and/or scaffold sequences. For example, the staple oligonucleotides are mixed in the appropriate quantities in an appropriate reaction volume. In preferred forms, the staple strand mixes are added in an amount effective to maximize the yield and correct assembly of the nanostructure. For example, in some forms, the staple strands are added in molar excess of the scaffold strand. In some forms, the staple strands are added in equimolar amounts to the scaffold strand. In particular forms, a disclosed nanostructure can be prepared by applying a temperature transition to a mixture of the scaffold strands, staple strands, and the linkers that make up the nanostructure, such that the strands and linkers anneal in appropriate fashion. In some forms, the temperature transition can occur over a period of 1-48 hours, inclusive, for example, 16 hours. In some forms, the temperature transition can involve a change in temperature from 90° C. to 20° C.

In some instances, the disclosed method of making a nanostructure can involve starting with a target design for the subunits based on a desired use for example. The nanostructure subunits can be produced using a four-step process. First, one or more computing devices are used to design the primary linear sequence of monomers for the nucleic acids that are to make up the nanostructure. Using known chemical and physical properties of the monomers (e.g., "normal" A:T and G:C nucleotide base pairing), the computing device(s) determines the appropriate sequences for each nucleic acid strand such that collectively their interactions produce subunits and/or nanostructures matching the shape and size of a particular design. Next, the polymers are independently fabricated using known techniques, such as in vitro chemical or biochemical synthesis (e.g., polymerase chain reaction synthesis of nucleic acids; in vitro transcription/translation) or in vivo biological synthesis (e.g., recombinant expression of nucleic acids and/or polypeptides). Next, the nucleic acid strands are allowed to form intra-molecular and/or inter-molecular bonds to create a subunit having the desired size and shape. In the formation step, each nucleic acid strand can be allowed to fold independently of the others, some can be allowed to fold together in the same environment, or all nucleic acid strands can be combined and allowed to fold together in the same environment. Preferably, all of the nucleic acid strands are combined, denatured, and then allowed to fold together, resulting in pre-determined inter- and intra-molecular bonding among all of the subunits. Finally, multiple subunits are combined under conditions that allow for specific, controlled binding of the subunits to the appropriate partners to form the nanostructure. It is to be understood that the subunits can have the same general structure or different structures. Preferably, all the subunits of a single nanostructure have the same structure (e.g., shape, size) and/or are identical (e.g., composed of the same nucleic acid strands in the same configuration).

In one exemplary form, disclosed are nucleic acid nanostructures fabricated from one or multiple nucleic acid strands, each of which has a primary nucleotide sequence that is engineered in conjunction with the sequences of the other nucleic acid strands of the nanostructure, if present. The collection of nucleic acid strands is engineered such that, when combined under conditions that permit annealing of the nucleic acid strands to themselves or, if present to other nucleic acid strands, they form into multiple, identical copies of a specific structure subunit, the finite size and shape of which are pre-determined by design. In the case where subunits are created, these then can be combined to form multiple, identical core subunits (e.g., a stack of subunits) of the nanostructures, the finite size and shape of which are pre-determined by design.

In another exemplary form, a 16 subunit (each containing, for example, 12 single-stranded DNA oligonucleotides) DNA mazzocchio nanostructure can be made by designing and synthesizing the DNA strands. The DNA can be purified by, for example, standard-desalting. The purified DNA oligonucleotides can be first diluted to a stock (e.g., 100 μM in nuclease free water). Equal amounts of each oligonucleotide can be mixed together in a buffer (e.g., in 20 mM Tris, 2 mM EDTA and 12.5 mM magnesium acetate) to achieve a final concentration of 7.5 μM for each oligonucleotide. The mixture can then be placed in a thermal cycler for a slow annealing process involving incubation at, for example, 90° C. for 5 minutes, and slow cooling from 90° C. to 20° C. at a rate of, for example, −0.1° C. per minute. Evaluation of the correct size of the DNA mazzocchio can be done by gel electrophoresis and transmission electron microscopy. Evaluation of the correct shape of the DNA mazzocchio can be done by transmission electron microscopy.

The resulting nanostructures can be characterized by standard techniques known in the art to be useful for nucleic acid nanostructures. These methods include, but are not limited to, polyacrylamide gel electrophoresis and agarose gel electrophoresis (which can be used to determine the correct interaction of the strands and to check the size of the final nanostructure), dynamic light scattering (which can be used to determine diameter and purity), and microscopic techniques such as electron microscopy, atomic force microscopy (AFM), and stochastic optical reconstruction microscopy (STORM). Stability can be assessed under culture conditions including nuclease rich serum and weak cationic solutions.

Subunits

The disclosed nanostructures are typically fabricated from multiple nucleic acid strands, which typically, but not necessarily, form multiple subunits that are ultimately combined to create a final core structure. For example, in some forms, the nanostructures can be composed of multiple subunits each having a defined polygonal shape in which the subunits are connected by linkers to form a structure having the continuous torus-like shape. In some forms, the subunits and linkers in the nanostructure form an extended supramolecular corkscrew. The polygon of each of the subunits can be of any shape. For example, the polygon of each of the subunits can be a hexagon, an octagon, a pentagon, a heptagon, a nonagon, a decagon, a quadrilateral (e.g., square, rectangle), or a triangle. Preferably, the polygon of each of the subunits is a hexagon or octagon.

In an exemplary form, multiple DNA strands are designed in conjunction with each other such that they interact in a specifically defined way via normal base pairing to form a pre-defined shape, such as a hexagon having fixed junctions/vertices. Each of the subunits can have multiple 5' and/or 3' overhangs that can serve as binding points for other subunits. Each overhang has a sequence that is designed to interact (e.g., hybridize) with only one other overhang of a designated subunit. In such a way, binding of subunits is completely controlled and the overall structure of the nanostructure can be designed by selection of the various sequences of the DNA strands making up the nanostructure.

The nanostructure can contain a plurality of subunits. For example, the nanostructure can contain hundreds of subunits (e.g., about 100, about 200, about 300, about 400, about 500, or more). In some forms, it can be preferable for the nanostructure to contain a smaller number subunits, such as less than 50 subunits for example. Preferably, a disclosed nanostructure can contain 8-40 subunits, inclusive (e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 subunits). Preferably, the disclosed nanostructures contain 16 or 32 subunits. Each subunit can contain 6-20 (e.g., 6, 7, 8, 9, 10, 11, 12, 13, 14, 15, 16, 17, 18, 19, 20) single-stranded nucleic acid strands (e.g., DNA strands). Preferably, each subunit contains 12 single nucleic acid strands.

In particular forms, each of the subunits can contain a core domain and a connecting domain, in which the core domain can define a polygon having a plurality of edges that enclose an open area, where the edges and open area define a plane of the subunit. A first edge of each subunit can be coplanar with the first edges of the other subunits, and each of the subunits can be between and connected to two other of the subunits with the planes of the connected subunits facing each other to form a stack of subunits. By analogy, a typical stack of dominos has the largest rectangular faces of the dominos facing each other. The planes of the connected subunits can be substantially perpendicular to the plane of the first edges of the subunits and tilted relative to the subunits connected to a given subunit in the direction horizontal to the plane of the first edges of the subunits. Substantially perpendicular refers to a perpendicular orientation within 100 of perpendicular, preferably within 5° of perpendicular, more preferably within 3° of perpendicular, and most preferably within 1° of perpendicular. The tilt between the planes of connected subunits can produce a curve in the stack of subunits such that the connected subunits form the continuous torus-like structure with a closed three-dimensional cavity defined by the open areas of the stacked subunits.

In some forms, the tilt and perpendicularity of the subunits relative to each other and to the plane of the first edges, respectively, can be varied. For example, by altering the tilt of the subunits plus or minus around the average tilt needed to close the torus-like shape, a waved or angled surface can be created (the wave being primarily in the top and bottom surface of the nanostructure). Similarly, by altering the perpendicularity of the subunits plus or minus around perfect perpendicularity, a waved or angled surface can be created (the wave being primarily in the outer and inner surface of the nanostructure). Combinations of both changes can create more varied and or more complex surfaces.

Scaffold Strands

In some forms, the disclosed nucleic acid nanostructures contain a plurality of subunits, where each of the subunits can contain a core domain and a connecting domain. Typically, the core domain of the subunits contains one scaffold nucleic acid strand, although more than one scaffold strand can be used for some designs.

In some forms, the basic technique for creating shapes for the subunits of the disclosed nanostructures involves folding a long single-stranded polynucleotide, referred to herein as a "scaffold strand", into a desired shape or structure using a number of small "helper strands" as glue to hold the scaffold in place. The number of helper strands will depend upon the size of the scaffold strand and the complexity of the shape or structure. The staple strands fix the scaffold strand into a particular pattern. The choice of staple strands determines the pattern.

The scaffold strand can be imagined as a long piece of string. To make a shape or structure, the scaffold strand is folded back and forth, in a raster pattern, to define the shape or structure. The resulting path that the scaffold strand takes is somewhat like a path in a maze; it typically does not cross itself. Each fold of the scaffold strand has a length which is a multiple of half turns of a polynucleotide (e.g., DNA) (about 5 or 6 nucleotides). Each fold occurs on a particular row in a shape or structure that is being created. If the fold is an even number of half turns the scaffold reverses direction in the shape/structure; if the fold is an odd number of half turns the scaffold continues the same direction in the shape/structure. These rules are typical for flat 2D structures, such as polygonal structures. For 3D structures the lengths of helices can be different. For example, to create a raster of the scaffold arrayed on a rectilinear 3D grid then the length of the scaffold can be in multiples of one-quarter (¼) turns. Similarly to create a raster of the scaffold on a hexagonally arrayed 3D grid the length of the scaffold can be in multiples of one-third (⅓) turns. By "arrayed on a type-X 3D grid," is meant that the positions of the centers of the helices in a cross-section of the nanostructure which is taken to be perpendicular to the set of parallel helices would lie a 2D pattern that could be aligned with a type-X 2D grid.

When the scaffold strand is folded into a shape or structure, certain sections of the scaffold are close together—sections that would be far away if the scaffold strand were completely stretched out. In some forms, when a computer program is used, for every short section of the scaffold strand (e.g., 8 bases), the program determines what other section of the scaffold should be nearby in the completed shape or structure. A computer program can then be used design helper strands to tie close or juxtaposed sections together. Imagine one section of a scaffold, strand 'A', that passes close to another section of a scaffold, strand 'B' (strands 'A' and 'B' can be the same of different scaffold strands). The program designs a helper strand so that half the helper strand binds 'A', and the other half of the helper strand binds 'B', when the helper strand binds both 'A' and 'B', the helper strand ties the strands together.

Given the folding path for the scaffold to form a desired shape or structure, the appropriate helper strands to hold it together are selected. For complex shapes, a computer program is typically used to select the helper strands. Helper strands are designed to hold two or more small sections or domains of the scaffold strand together.

The length of the scaffold strand can vary depending on the desired size and shape of the polygon that it will be folded into. Typically, scaffold strands include between 10 and 1000 nucleotides, for example, about 10, 20, 30, 40, 50, 60, 70, 80, 90, 100, 150, 200, 250, 300, 350, 400, 450, 500, 600, 700, 800, 900, or 1000 nucleotides. In particular forms, the scaffold strand includes about 70-560 nucleotides, inclusive. For example, the scaffold strand can include about 70-100, 100-150, 150-200, 200-250, 250-300, 300-350, 350-400, 400-450, 450-500, or 500-560 nucleotides, inclusive.

The scaffold strand can be derived from any natural or artificial source. In some forms, the scaffold strand is derived from a phage genome. In some forms, the scaffold strand is derived from a segment of an M13 viral genome. In some forms, the scaffold strand is derived from M13mp18 single-stranded DNA. Other single-stranded circular DNA that can be used to fold a subunit of a DNA nanostructure include, without limitation, p7308, p7560, p7704, p8064, p8634, and pEGFP. In some forms, the scaffold strand can contain an arbitrary sequence and/or can be produced by chemical synthesis based on methods standard in the art (e.g., solid phase synthesis, PCR assembly). See for example, Hughes R A., et al., *Cold Spring Harb. Perspect. Biol.* 9(1). pii: a023812 (2017).

Staple Strands

In some forms, the disclosed nanostructures use short "staple" strands or "helper strands" of nucleic acids to fix a polynucleotide strand into a particular pattern. The choice of staple strands determines the pattern. In one form, a software program can be used to identify the staple strands needed to form a given design.

Typically, when staple strands are employed, the number of staple strands will depend upon the size of the scaffold strand and the complexity of the shape or structure. For example, for relatively short scaffold strands (e.g., about 50 to 1,500 base in length) and/or simple structures the number of staple strands can be small (e.g., about 2, 3, 4, 5, 6, 7, 8, 9, 10, 11, 12, 13, 14, 15, 16, 17, 18, 19, 20, 30, 40, 50, or more). For longer scaffold strands (e.g., greater than 1,500 bases) and/or more complex structures, the number of staple strands can be several hundred to thousands (e.g., 50, 100, 300, 600, 1,000 or more helper strands).

Typically, staple strands include between 10 and 600 nucleotides, for example, 14-600 nucleotides. In particular forms, the staple strands include about 13-219 nucleotides, inclusive. For example, in some forms, one or more staple strands can include about 10, 20, 30, 40, 50, 60, 70, 80, 90, 100, 120, 140, 160, 180, 200, 220, 240, 260, 280, 300, 350, 400, 450, 500, 550, or 600 nucleotides. In some forms, each staple strand includes a central region flanked by a 3' overhang region, a 5' overhang region, or both. Preferably, the central region of the staple strand is flanked by both the 3' overhang region and the 5' overhang region. The central region of each staple strand can bind to the scaffold strand to form a duplex region. The 5' overhangs of the staple strands can each individually contain any number of nucleotides (e.g., 1, 2, 3, 4, 5, 6, 7, 8, 9, 10, 11, 12, 13, 14, 15, 16, 17, 18, 19, 20 or more), the 3' overhangs of the staple strands can each individually contain any number of nucleotides (e.g., 1, 2, 3, 4, 5, 6, 7, 8, 9, 10, 11, 12, 13, 14, 15, 16, 17, 18, 19, 20 or more), or both. In preferred forms, the 5' overhangs of the staple strands can each individually contain 8-16 nucleotides, inclusive, the 3' overhangs can each individually contain 8-16 nucleotides, inclusive, or both. It can be appreciated that on any given strand, the 5' overhang and 3' overhang can contain the same or different number of nucleotides.

Staple strands are typically provided in a folding buffer. The staple strands are typically, but not necessarily, added to the single-stranded scaffold sequence in equimolar amounts, in combination with appropriate salts and detergents.

Linker Strands

Each of the subunits in a given nanostructure can contain a core domain and a connecting domain. The connecting domain of each subunit can contain one or more linkers (also referred to as linker strands) and the connection between the subunits can be made by the linkers. Such connections can involve nucleic acid based hybridization between linkers and overhangs on the scaffold strands and/or staple strands of the core domains.

The number of linkers comprising the connecting domain of a subunit can vary. For example, without limitation, a connecting domain can contain 3-20 linkers, inclusive. In some forms, the number of linkers can depend on the particular polygon defined by the subunit of the core domain. For example, in some forms, a connecting domain can have six linkers for a hexagonal subunit, eight linkers for an octagonal subunit, and ten linkers for a decagonal subunit. In some forms, the connecting domain of the subunits contains n linker strands, where n is the number of sides in the polygons of the subunits or the number of vertices in the polygons of the subunits.

Each linker can have a length configured to create the tilt between the planes of connected subunits such that the continuous torus-like structure of the nanostructure is produced. The length of each linker, and the place of that linker in the subunit, sets the spacing between the place where the linker is attached to its subunit and the place where its complementary linker attaches to its subunit. Since each of the linker lengths can be varied by design, the tilt, spacing, and perpendicularity of the subunits can be designed and selected to define and establish the overall structure and shape of the nanostructure. Such design is what is meant, in part, by configuration of the linkers. As such, in any given subunit, one or more linker strands can be of the same or different lengths. Typically, linker strands include between 2 and 600 nucleotides, inclusive. For example, linker strands can include 2-20, 15-50, 40-100, 80-300, 200-600 nucleotides inclusive. In particular forms, the linker strands include about 2-60 (e.g., 2-58) nucleotides, inclusive. Within a given subunit, all of the linkers can be unique in sequence.

Typically, the linkers are complementary to one or more overhang regions of the core domain. Typically, hybridization of various strands and complementarity therein is based on Watson-Crick base pairing. The degree of complementarity (number of complementary residues) between one or more linkers of the connecting domain and overhang regions of the core domain can be 16-32 base pairs, inclusive. The subunits and linkers in the nanostructure form an extended supramolecular corkscrew.

Upon hybridization, the linkers and the overhangs can be completely, substantially, or partially double stranded. For complete or substantial double strandedness, the length of the linkers will be the same or nearly the same as the overhangs to which they are complementary. This is the preferred design. For partial double strandedness, the length of the linkers can be either longer than or shorter than the overhangs to which they are complementary. Alternatively, the linkers can have some sequences that are not complementary to their corresponding overhangs (as well as sequences that are complementary to the overhangs). In these ways, the length of the linkers can influence or determine the length of the overhangs. It will be understood that where the linkers and their corresponding overhangs are only partially complementary, the effective length of the linkers and overhangs should be considered in designing the spacing between subunits and the length of the linkers.

For example, particularly when the subunit defines a hexagon, the core domain can contain 6 nucleic acid strands (strands 1-6) and the connecting domain can contain six single-stranded nucleic acid linkers (strands 7-12) that are complementary to one or more overhang regions of the core domain. In this form, strand 8 of the connecting domain can be arranged to be complementary to the 5' overhang of strand 1 of a first subunit and the 3' overhang of strand 1 from another subunit. The degree of complementarity between strand 8 and the 5' and 3' overhangs of strand 1 can be 28 base pairs (i.e., strand 8 is completely complementary). Strand 9 of the connecting domain can be arranged to be complementary to the 5' overhang of strand 2 and 3' overhang of strand 3 of the core domain and the degree of complementarity can be 20 base pairs. Strand 10 of the connecting domain can be arranged to be complementary to 5' overhang of strand 3 and 3' overhang of strand 4 of the core domain and the degree of complementarity can be 16 base pairs. Strand 11 of the connecting domain can be arranged to be complementary to 5' overhang of strand 4 and 3' overhangs of strand 5 of the core domain and the degree of complementarity can be 20 base pairs. Strand 12 of the connecting domain can be arranged to be complementary to 5' overhang of strand 5 and 3' overhang of strand 6 of the core domain and the degree of complementarity can be 28 base pairs. Strand 7 of the connecting domain can be arranged to be complementary to 5' overhang of strand 6 and 3' overhang of strand 2 of the core domain, and the degree of complementarity can be 32 base pairs.

Shape and Size

The disclosed nucleic acid nanostructures can contain a plurality of subunits, in which the nanostructures have a continuous torus-like structure with a closed three-dimensional cavity. Each of the subunits can contain a core domain and a connecting domain, in which the core domain can define a polygon having a plurality of edges that enclose an open area. The core domains of the subunits of the nucleic acid nanostructures can have any arbitrary geometric shape and size. Several variants of geometries are contemplated herein for construction of nucleic acid nanostructures. In some forms, the polygon of each of the subunits can be a hexagon, an octagon, a pentagon, a heptagon, a nonagon, a decagon, a quadrilateral (e.g., square, rectangle), or a triangle. In preferred forms, the core domain can define a hexagon or octagon. Any methods for the manipulation, assortment or shaping of nucleic acids can be used to produce the nanostructure subunits. Typically, the methods include methods for "shaping" or otherwise changing the conformation of nucleic acid, such as methods for DNA origami.

It will be appreciated that generally, the core domain of the subunits contains one scaffold nucleic acid strand and n−1 staple nucleic acid strands, where n is the number of sides in the polygons of the subunits. For example, a subunit having an octagonal shape would contain a core domain having one scaffold strand and seven staple strands.

The disclosed nanostructures can have a continuous torus-like structure with a closed three-dimensional cavity defined by the open areas of the stacked subunits contained therein. The size of the cavity is therefore defined by the open area enclosed by the edges of the subunits. The open area can be any desired size. In some forms, the open area can be any size to accommodate the encapsulation of any cargo of interest. In some forms, the dimension of the open area is in the range of about 30-2165 nm², inclusive. This dimension (30-2165 nm²) can be particularly optimal for mazzocchio nanostructures having hexagonal subunits.

In particular forms, mazzocchio based nanostructures can have a circumference of about 157-314 nm, inclusive.

In some forms, the dimension of an edge of the open area is less than 100 nm, preferably less than 50 nm, more preferably less than 20 nm, most preferably less than 15 nm. In some forms, the subunit of the nanostructure contains a polygon have one or more edges having a dimension of 5-200 nm, such as 5, 10, 15, 20, 30, 35, 40, 45, 50, 55, 60, 65, 70, 75, 80, 85, 90, 95, 100, 105, 110, 115, 120, 125, 130, 135, 140, 150, 155, 160, 165, 170, 175, 180, 185, 190, 195, or 200 nm. In some forms, each edge of a polygon has a dimension of 5-200 nm, such as 5, 10, 15, 20, 30, 35, 40, 45, 50, 55, 60, 65, 70, 75, 80, 85, 90, 95, 100, 105, 110, 115, 120, 125, 130, 135, 140, 150, 155, 160, 165, 170, 175, 180, 185, 190, 195, or 200 nm.

In some forms, the polygonal diameter can be 5-200 nm, such as 5, 10, 15, 20, 30, 35, 40, 45, 50, 55, 60, 65, 70, 75, 80, 85, 90, 95, 100, 105, 110, 115, 120, 125, 130, 135, 140, 150, 155, 160, 165, 170, 175, 180, 185, 190, 195, or 200 nm. Preferably, the polygonal diameter is 50-100 nm. In some forms, the polygonal diameter is less than 100 nm, preferably less than 50 nm, more preferably less than 20 nm, most preferably less than 15 nm.

The enclosed 3D cavity of the nanostructure is a hollow, open space enclosed within the torus-like ring that can contain the cargo of interest. This cavity will typically have dimensions smaller than those of the overall nanostructure. In some cases, a disclosed nanostructure encapsulates a cargo of interest within the cavity of the torus-like ring. Any compound having any purpose or function can be encapsulated as cargo within the cavity. Exemplary cargo include, without limitation, small molecules, lipids, proteins, enzymes, antibodies, protein complexes, phospholipids, nucleic acids, and combinations thereof.

ii. Nucleotide Modifications

In some forms, the nucleotide sequences of the nanostructures are modified. For example, in some forms, one or more of the nucleotides of the staple strands are modified, or one or more of the nucleotides of scaffold strands are modified, or one or more of the nucleotides of the linker strands are modified or combinations thereof.

When modified nucleotides are incorporated into nucleic acid scaffold strands, linker strands, and/or staple strands, the modified nucleotides can be incorporated as a percentage or ratio of the total nucleotides used in the preparation of the nucleic acids. In some forms, the modified nucleotides represent 0.1% or more than 0.1% of the total number of nucleotides in the sequence, up to or approaching 100% of the total nucleotides present. For example, the relative amount of modified nucleotides can be between 0.1% and 100% inclusive, such as 0.1%-0.5%, 1%-2%, 1%-5%, 1%-10%, 10%-20%, 20%-30%, 30%-40%, 40%-50%, or more than 50% of the total, up to and including 100%, such as 60%, 70%, 75%, 80%, 85%, 90%, 95% or 99% of the total. In some forms, a sequence of nucleic acids includes a single modified nucleotide, or two, or three modified nucleotides.

In some forms, nucleic acid nanostructures contain modified nucleotides at precise locations and in specific numbers or proportions as determined by the design process. Therefore, in some forms, nucleic acid nanostructures can include a defined number or percentage of modified nucleotides at specified positions within the structure. In some forms, nucleic acid nanostructures include more than a single type of modified nucleic acid.

Non-naturally occurring nucleic acids can include, for example, mixtures of naturally and non-naturally occurring nucleotides. Non-naturally occurring nucleotides and/or nucleotide analogs can be modified at the ribose, phosphate, and/or base moiety. In some forms, nucleic acids can comprise ribonucleotides and non-ribonucleotides. In some such forms, nucleic acids can comprise one or more ribonucleotides and one or more deoxyribonucleotides. In some forms, nucleic acids can comprise one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, peptide nucleic acids (PNA), bridged nucleic acids (BNA), or morpholinos. Other examples of modified nucleotides include 2'-O-methyl analogs, 2'-deoxy analogs, 2-thiouridine analogs, N6-methyladenosine analogs, or 2'-fluoro analogs. Further examples of modified nucleotides include linkage of chemical moieties at the 2' position, including but not limited to peptides, nuclear localization sequence (NLS), peptide nucleic acid (PNA), morpholino, polyethylene glycol (PEG), triethylene glycol, or tetraethyleneglycol (TEG). Further examples of modified bases include, but are not limited to, 2-aminopurine, 5-bromouridine, pseudouridine ($\Psi$), $N^1$-methylpseudouridine ($me^1\Psi$), 5-methoxyuridine (5moU), inosine, 7-methylguanosine. Examples of nucleic acid chemical modifications include, without limitation, incorporation of 2'-O-methyl (M), 2'-O-methyl-3'-phosphorothioate (MS), phosphorothioate (PS), S-constrained ethyl (cEt), 2'-O-methyl-3'-thioPACE (MSP), or 2'-O-methyl-3'-phosphonoacetate (MP) at one or more terminal nucleotides. Such chemically modified nucleic acids can comprise increased stability as compared to unmodified nucleic acids.

Examples of modified nucleotides that can be included within the described nanostructures include, but are not limited, to diaminopurine, $S^2T$, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and (acp3)w, 2,6-diaminopurine. Nucleic acid molecules can also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules can also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

In some forms, phosphorothioate modified backbone on the DNA nucleotide of scaffold, staple, and/or linker strands is used to improve stability of the nanostructures (e.g., to resist degradation by exonucleases). For example, in some forms, the nucleic acid nanostructures include modified nucleic acids that protect one or more regions of the structure from enzymic degradation or disruption in vivo. In this way, modifications can enhance protection to enzymatic degradation of one or more parts of a nanostructure in vivo, for example to enhance or alter the half-life of a given structure in vivo.

Locked nucleic acid (LNA) is a family of conformationally locked nucleotide analogues which, amongst other benefits, imposes truly unprecedented affinity and very high nuclease resistance to DNA and RNA oligonucleotides (Wahlestedt C, et al., *Proc. Natl Acad. Sci. USA,* 975633-5638 (2000); Braasch, D A, et al., *Chem. Biol.* 81-7 (2001); Kurreck J, et al., *Nucleic Acids Res.* 301911-1918 (2002)). In some forms, the nanostructures contain synthetic RNA-like high affinity nucleotide analogue, locked nucleic acids. In some forms, the scaffold strands, staple strands, and/or linker strands are synthetic locked nucleic acids.

Peptide nucleic acid (PNA) is a nucleic acid analog in which the sugar phosphate backbone of natural nucleic acid has been replaced by a synthetic peptide backbone usually formed from N-(2-amino-ethyl)-glycine units, resulting in an achiral and uncharged mimic (Nielsen, et al., *Science* 254, 1497-1500 (1991)). It is chemically stable and resistant to hydrolytic (enzymatic) cleavage. In some forms, the nanostructures contain PNAs. In some forms, the scaffold strands, staple strands, and/or linker strands are PNAs.

In some forms, a combination of PNAs, DNAs, and/or LNAs is used for the nucleic acids of the nanostructures. For example, in some forms, a combination of PNAs, DNAs, and/or LNAs is used for the staple strands, linker strands, scaffold strands, and/or any nucleic acid component of the nanostructure.

In some forms, nucleic acid can comprise morpholino oligonucleotides. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

One of skill in the art will recognize that the disclosed nanostructures can contain various combinations of the described modified or unmodified nucleic acids. For example, the disclosed nanostructures can contain DNA, RNA, LNA, PNA, or combinations thereof. As such, it is to be understood that the nucleic acids used in the disclosed compositions and methods can be homogeneous or heterogeneous in nature. As an example, nucleic acids can be completely DNA in nature or they can include DNA and non-DNA (e.g., LNA) monomers or sequences.

C. Cargo

The disclosed nucleic acid nanostructures are useful for carrying, presenting, and/or delivering cargo. The nanostructures are suitable as a delivery vehicle for cargo including therapeutic, prophylactic and/or diagnostic agents. The nanostructure can contain one or more types of cargo. The cargo can be covalently or non-covalently bound to the nanostructure. The cargo can be encapsulated within the nanostructure. It will be appreciated that the disclosed torus-like nanostructures (e.g., DNA mazzocchio) contain two distinct spaces: (1) the hole at the center of the "doughnut" and (2) the closed cavity within the tube of the continuous torus-like structure. As such, cargo can be loaded in either one, or both of these spaces.

Since the nanostructures are nucleic acid based, DNA nanostructures are entirely biocompatible and elicit minimal immune response in the host. The design of any desired geometry of DNA nanostructure further allows manipulation of DNA structure tailored for individual drugs, dose, site of target and desired rate of degradation etc.

Any cargo can be incorporated into the nucleic acid nanostructures either directly or indirectly, via a variety of interactions, non-covalent or covalent. Some exemplary non-covalent interactions for attachment include intercalation, biotin-streptavidin interaction, chemical linkers (e.g., using Click-chemistry groups), and hybridization between complementary nucleotide sequences (i.e., base pairing). In some forms, the incorporation or loading of a cargo into the nanostructure can involve the formation of a bond, such as a covalent bond (e.g., carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g., complexation or chelation between metal ions and monodentate or multidentate ligands), or the like. Cargo incorporation can also involve hydrophobic interactions or van der Waals interactions. In some forms, the incorporation or loading of a cargo into the nanostructure can involve maleimide thiol coupling.

The nanostructure can include one or more linking/adaptor moieties for linking the cargo to the nanostructure. Non-limiting examples of linking/adaptor moieties include avidin, neutravidin, streptavidin, biotin, and any other suitable crosslinking molecules. The nanostructures can be functionalized using any suitable chemical modifications to allow for incorporation of a cargo. An example is a copper-free click chemistry that can be used to functionalize the nanostructure to bind any cargo, including linkers, peptides, antibodies, and fluorescent or radiolabeled reporter molecules.

In some forms, the agents to be delivered are simply captured inside the nanostructures, for example, inside the hole at the center of the "doughnut". In these cases, pore size of the nanostructure is an important consideration, i.e., they are small enough so that the cargo captured does not leak out. In some forms, the DNA mazzocchio are assembled in pieces to allow the capture of cargo prior to the completion of the nanostructures.

In some forms, two or more cargo can be physically entrapped, encapsulated, and/or non-covalently associated with the nanostructures. One agent can potentiate the efficacy of another encapsulated agent. One of skill in the art will appreciate that an agent, molecule, moiety, or compound described within a certain class (e.g., diagnostic agent) is not limited to that class. An agent, molecule, moiety, or compound can serve multiple functions and therefore can serve as more than one type of cargo, unless otherwise indicated. For example, the same molecule can be a diagnostic agent, an imaging agent, a therapeutic agent, a prophylactic agent, or a toxic agent.

In yet another form, the nanostructure compositions include a mixture of agents (e.g., a cocktail of proteins) for continuous delivery to a tissue or a cell in need thereof.

Cargo for the disclosed nanostructures can be any molecules, materials, and compositions desired to be carried, presented, and/or delivered by the disclosed nucleic acid nanostructures. The disclosed cargos can be combined, linked and/or coupled in any suitable manner. For example, agents and other molecules can be associated covalently or non-covalently, directly or indirectly, with or without a linker moiety. In some forms, the cargo can include therapeutic, prophylactic, toxic, diagnostic, or other agents. Exemplary agents for use as cargo include proteins, peptides, carbohydrates, nucleic acid molecules, polymers, small molecules, and combinations thereof. In some forms, the cargo can include a peptide drug, a dye, an antibody, or antigen-binding fragment of an antibody. Therapeutic agents for use as cargo can include anti-cancer, anti-inflammatories, or more specific drugs for inhibition of a disease or disorder to be treated. Genetic therapeutics for use as cargo can include anti-sense DNA and RNA as well as DNA coding for proteins, mRNA, miRNA, piRNA and siRNA.

In particular forms, the disclosed nanostructures contain a therapeutic, toxic, targeting, imaging, diagnostic or prophylactic agent, or combinations thereof. In particular forms, the nanostructures contain an imaging agent including, but not limited to, a gold nanoparticle. In particular forms, the disclosed nanostructures can contain a targeting agent including, but not limited to, an aptamer. In particular forms, the disclosed nanostructures contain a molecule such as DNA, RNA, PNA, protein, peptide, lipid, carbohydrate, a small-molecule, or a dye. The agent or molecule can be covalently or non-covalently bound to the nanostructure. In some forms, the agent or molecule can be encapsulated within the nanostructure.

1. Targeting Agents

In some forms, the nanostructures comprise one or more targeting agents (also referred to herein as targeting molecules) that can specifically target the nucleic acid nanostructure to one or more types of cells, tissues, organs, or microenvironments relative to other types of cells, tissues, organs, or microenvironments in vivo, or to mediate specific binding to a protein, lipid, polysaccharide, nucleic acid, etc. In some forms, the targeting agents can specifically target the nucleic acid nanostructures to one or more subcellular compartments.

Exemplary targeting agents include proteins, peptides, nucleic acids, lipids, saccharides, or polysaccharides that bind to one or more targets associated with an organ, tissue, cell, or extracellular matrix, or specific type of tumor or infected cell. The degree of specificity with which the nucleic acid nanostructures are targeted can be modulated through the selection of a targeting molecule with the appropriate affinity and specificity. For example, antibodies, or antigen-binding fragments thereof are very specific.

Typically, the targeting agents exploit the surface-markers specific to a biologically functional class of cells, such as antigen presenting cells. For example, dendritic cells express a number of cell surface receptors that can mediate endocytosis. In some forms, overhang sequences include nucleotide sequences that are complementary to nucleotide sequences of interest, for targeting purposes. In some forms, the disclosed nanostructures can be targeted via lectin-mediated endocytosis.

Additional functional groups can be introduced on the staple strand for example by incorporating biotinylated nucleotide into the staple strand. Any streptavidin-coated targeting molecules are therefore introduced via biotin-streptavidin interaction. In other forms, non-naturally occurring nucleotides are included for desired functional groups for further modification. Exemplary functional groups include targeting agents, immunomodulatory elements, chemical groups, biological macromolecules, and combinations thereof.

In some forms, the targeting molecules can be antibodies or fragments thereof, ligands for specific receptors, or other proteins specifically binding to the surface of the cells to be targeted. Other non-limiting examples molecules include peptides, affinity ligands, cell penetrating molecules, endosomal escape molecules, subcellular targeting molecules, nuclear targeting molecules.

Examples of subcellular targeting molecules are described in, for example, U.S. Patent Application Publication Nos. 2009031733, 20090258926, 20090176660, 20080311136, 20070287680, 20070157328, 20070111270, 20070111251, 20060257942, 20060154340, 20060014712, 20050281805, 20050233356, 20040005309, 20030082176, and 20010021500, which are hereby incorporated by reference in their entirety and specifically for their description of subcellular targeting molecules and motifs. Examples of nuclear targeting molecules are described in, for example, U.S. Patent Application Publication Nos. 10100143454, 20100099627, 20090305329, 20090176710, 20090087899, 20070231862, 20070212332, 20060242725, 20060233807, 20060147922, 20060070133, 20060051315, 20050147993, 20050071088, 20030166601, 20030125283, 20030083261, 20030003100, 20020068272, and 20020055174, which are hereby incorporated by reference in their entirety and specifically for their description of nuclear targeting molecules and motifs.

i. Antibodies

In some forms, nucleic acid nanostructures are modified to include one or more antibodies. Antibodies that function by binding directly to one or more epitopes, other ligands, or accessory molecules at the surface of cells can be coupled directly or indirectly to the nanostructures. In some forms, the antibody or antigen binding fragment thereof has affinity for a receptor at the surface of a specific cell type, such as a receptor expressed at the surface of macrophage cells, dendritic cells, or epithelial lining cells. In some forms, the antibody binds one or more target receptors at the surface of a cell that enables, enhances or otherwise mediates cellular uptake of the antibody-bound nanostructure, or intracellular translocation of the antibody-bound nanostructure, or both.

Any specific antibody can be used to modify the nucleic acid nanostructures. For example, antibodies can include an antigen binding site that binds to an epitope on the target cell. Binding of an antibody to a "target" cell can enhance or induce uptake of the associated nucleic acid nanostructures by the target cell protein via one or more distinct mechanisms.

In some forms, the antibody or antigen binding fragment binds specifically to an epitope. The epitope can be a linear epitope. The epitope can be specific to one cell type or can be expressed by multiple different cell types. The antibody or antigen binding fragment thereof can bind a conformational epitope that includes a 3-D surface feature, shape, or tertiary structure at the surface of the target cell.

In some forms, the antibody or antigen binding fragment that binds specifically to an epitope on the target cell can only bind if the protein epitope is not bound by a ligand or small molecule.

Various types of antibodies and antibody fragments can be used to modify nucleic acid nanostructures, including whole immunoglobulin of any class, fragments thereof, and synthetic proteins containing at least the antigen binding variable domain of an antibody. The antibody can be an IgG antibody, such as IgG1, IgG2, IgG3, or IgG4 subtypes. An antibody can be in the form of an antigen binding fragment including a Fab fragment, F(ab')2 fragment, a single chain variable region, and the like. Antibodies can be polyclonal, or monoclonal (mAb). Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison, et al., *Proc. Natl. Acad. Sci. USA*, 81: 6851-6855 (1984)). The antibodies can also be modified by recombinant means, for example by deletions, additions or substitutions of amino acids, to increase efficacy of the antibody in mediating the desired function. Substitutions can be conservative substitutions. For example, at least one amino acid in the constant region of the antibody can be replaced with a different residue (see, e.g., U.S. Pat. Nos. 5,624,821; 6,194,551; WO 9958572; and Angal, et al., *Mol. Immunol.* 30:105-08 (1993)). In some cases changes are made to reduce undesired activities, e.g., complement-dependent cytotoxicity. The antibody can be a bi-specific antibody having binding specificities for at least two different antigenic epitopes. In some forms, the epitopes are from the same antigen. In some forms, the epitopes are from two different antigens. Bi-specific antibodies can include bi-specific antibody fragments (see, e.g., Hollinger, et al., *Proc. Natl. Acad. Sci. U.S.A.*, 90:6444-48 (1993); Gruber, et al., *J. Immunol.*, 152:5368 (1994)).

Antibodies that target the nucleic acid nanostructures to a specific epitope can be generated by any means known in the art. Exemplary descriptions means for antibody generation and production include Delves, Antibody Production: Essential Techniques (Wiley, 1997); Shephard, et al., Monoclonal Antibodies (Oxford University Press, 2000); Goding, Monoclonal Antibodies: Principles and Practice (Academic Press, 1993); and Current Protocols in Immunology (John Wiley & Sons, most recent edition). Fragments of intact Ig molecules can be generated using methods well known in the art, including enzymatic digestion and recombinant means.

ii. Aptamers

In some forms, nanostructures described herein are conjugated with or incorporate nucleic acid-based aptamers which can contribute to their preferential targeting to one or more types of cells, tissues, organs, or microenvironments. In some forms, the aptamer can enhance internalization of the nanostructure into a cell (e.g., if the aptamer binds to a cell-surface marker).

Aptamers are short single-stranded DNA or RNA oligonucleotides (6-26 kDa) that fold into well-defined 3D structures that recognize a variety of biological molecules including transmembrane proteins, sugars and nucleic acids with high affinity and specificity (Yu B, et al., *Mol Membr Biol.,*

27(7):286-98 (2010)). The high sequence and conformational diversity of naïve aptamer pools (not yet selected against a target) makes the discovery of target binding aptamers highly likely. Aptamers preferably interact with a target molecule in a specific way. Typically aptamers are small nucleic acids ranging from 15-50 bases in length that fold into defined secondary and tertiary structures, such as stem-loops or G-quartets. Aptamers can bind small molecules, such as ATP and theophylline, as well as large molecules, such as reverse transcriptase and thrombin. Aptamers can bind very tightly to the target molecule, with Kds of less than $10^{-12}$ M. It is preferred that the aptamers bind the target molecule with a Kd less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a Kd with the target molecule at least 10, 100, 1000, 10,000, or 100,000 fold lower than the Kd with a background binding molecule. It is preferred when doing the comparison for a molecule such as a polypeptide, that the background molecule be a different polypeptide.

In some forms, the aptamer specifically binds to surface or transmembrane proteins, such as, for example, integrin $\alpha v \beta 3$, VEGF receptor, EGF receptor, HER2, HER3, MUC1, PSMA, and receptor tyrosine kinase RET. The aptamer can comprise modified or unmodified DNA or RNA. In some forms, the aptamers are nuclease resistant. In some forms, the aptamer is an RNA aptamer that is 2'-modified (e.g., 2'-fluro and 2'-O-methyl). Non-limiting examples of aptamers contemplated for use in the disclosed compositions and methods that have been recently used to target assemblies are provided in Friedman A D, et al., *Curr Pharm Des.*, 19(35):6315-29 (2013) (see Table 7). In some forms, one or more of the following aptamers can be used as targeting agents on the provided nanostructures: Sgc8c PTK7 aptamer, S2.2 MUC-1 aptamer, and AS1411 nucleolin aptamer.

In some forms, an aptamer can be directly appended onto an end of one of the sequences which are integral in the scaffold (e.g., 3' or 5' end of any strand in the subunit, such as a linker strand) such that it would raise out from the surface. For example, in a specific form, an aptamer (e.g., a single-stranded DNA aptamer) can be appended to the 3' end of strand 7 of one or more hexagonal subunits in a DNA nanostructure (e.g., DNA mazzocchio). In this form, the aptamer will be displayed on the outer-surface of the nanostructure. In other forms of the nanostructures, the aptamer can be appended to analogous ends of analogous strands such that the aptamer can raise out the surface. It is contemplated that this design renders the aptamer more robust to the cellular milieu although the aptamer can be somewhat hidden from its target. In some forms, an adaptor sequence can be appended to the aptamer then a stretch of base-pairing can be used to append the aptamer onto the nanostructure. It is contemplated that in this design, the aptamer can be more exposed to its target but can be less robust to nucleases in the environment.

iii. Lectins

Lectins that can be covalently attached to nucleic acid nanostructures to render them target specific to the mucin and mucosal cell layer include lectins isolated from *Abrus precatroius, Agaricus bisporus, Anguilla, Arachis hypogaea, Pandeiraea simplicifolia, Bauhinia purpurea, Caragan arobrescens, Cicer arietinum, Codium fragile, Datura stramo-*

*nium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius*, and *Lotus tetragonolobus.*

The choice of targeting molecule will depend on the method of administration of the nanostructure composition and the cells or tissues to be targeted. The targeting molecule can generally increase the binding affinity of the nanostructures for cell or tissues or can target the assembly to a particular tissue in an organ or a particular cell type in a tissue.

2. Imaging and Diagnostic Agents

In some forms, the nanostructures comprise one or more imaging agents. In some forms, the nanostructures comprise one or diagnostic agents. An agent can be both an imaging agent and a diagnostic agent. As used herein, the term "imaging agent" refers to any molecule which can be detected through a variety of techniques. Useful imaging agents include moieties that can be administered in vivo and subsequently detected.

In some forms, the disclosed nanostructures contain a gold nanoparticle as an imaging agent. In some forms, the gold nanoparticle is contained within (1) the hole at the center of the "doughnut", (2) within the closed cavity within the tube of the continuous torus-like structure, or (3) both.

The cargo imaging or diagnostic agent can be an isotope. Such isotopes can be useful, for example, as a therapeutic agent, as a detectable agent, or both. Examples of useful isotopes include Lutetium-177 ($^{177}$Lu), Rhenium-188 ($^{188}$Re), Gallium-68 ($^{68}$Ga), Yttrium-90 ($^{90}$Y), Technetium-99m ($^{99m}$Tc), Holmium-166 ($^{166}$Ho), Iodine-131 ($^{131}$I) Indium-111 ($^{111}$In), Flourine-18 ($^{18}$F), Carbon-11 ($^{11}$C), Nitrogen-13 ($^{13}$N), Oxygen-15 ($^{15}$O), Bromine-75 ($^{75}$Br), Bromine-76 ($^{76}$Br), Iodine-124 ($^{124}$I), Thalium-201 ($^{201}$Tl), Technetium-99 ($^{99}$Tc), and Iodine-123 ($^{123}$I)

Imaging agents useful in the disclosed compositions and imaging methods include, yet are not limited to, dyes, radiolabels and fluorescent molecules. The imaging agent can be, for example, any moiety that facilitates detection, either directly or indirectly, preferably by a non-invasive and/or in vivo visualization technique. For example, an imaging agent can be detectable by any known imaging techniques, including, for example, a radiological technique. Imaging agents can include, for example, a contrast agent. The contrast agent can be, for example, Feridex. In some forms, for instance, the imaging agent comprises a tantalum compound. In some forms, the imaging agent comprises iodine, such as radioactive iodine. In some forms, for instance, the imaging agent comprises an organic iodo acid, such as iodo carboxylic acid, triiodophenol, iodoform, and/or tetraiodoethylene. In some forms, the imaging agent comprises a non-radioactive detectable agent, e.g., a non-radioactive isotope. For example, iron oxide and Gd can be used as a non-radioactive imaging agent in certain forms. Imaging agents can also include radioactive isotopes, enzymes, fluorophores, and quantum dots (Qdot®). For example, the detection moiety can be an enzyme, biotin, metal, or epitope tag. Other known or newly discovered detectable markers are contemplated for use as imaging agents with the provided nanostructures. In some forms, for instance, the imaging agent comprises a barium compound, e.g., barium sulfate.

Examples of imaging agents include radiologic contrast agent, such as diatrizoic acid sodium salt dihydrate, iodine, and barium sulfate, a fluorescing imaging agent, such as Lissamine Rhodamine P E, a fluorescent or non-fluorescent stain or dye, for example, that can impart a visible color or that reflects a characteristic spectrum of electromagnetic radiation at visible or other wavelengths, for example, infrared or ultraviolet, such as Rhodamine, a radioisotope, a positron-emitting isotope, such as $^{18}$F or $^{124}$I (although the short half-life of a positron-emitting isotope can impose some limitations), a metal, a ferromagnetic compound, a paramagnetic compound, such as gadolinium, a superparamagnetic compound, such as iron oxide, and a diamagnetic compound, such as barium sulfate. Imaging agents can be selected to optimize the usefulness of an image produced by a chosen imaging technology. For example, the imaging agent can be selected to enhance the contrast between a feature of interest, such as a gastrointestinal polyp, and normal gastrointestinal tissue.

Imaging can be accomplished using any suitable imaging techniques such as X-Ray, computed tomography (CT), MRI, Positron Emission Tomography (PET) or SPECT. In some forms, the nanostructure can be coupled to a nuclear medicine imaging agent such as Indium-III or Technetium-99, to PET imaging agents, or to MRI imaging agents such as nanoparticles.

Examples of imaging techniques include magnetic resonance imaging (MRI), computerized tomography (CT), single photon emission computerized tomography (SPECT), and positron emission tomography (PET). Imaging agents generally can be classified as either being diagnostic or therapeutic in their application. Therefore, imaging agents and diagnostic agents can encompass the same agents, moieties, or compounds. Because of radiation's damaging effect on tissues, it is useful to target the biodistribution of radiopharmaceuticals as accurately as possible. PET can use imaging agents labeled with, for example, the positron-emitters such as $^{18}$F, $^{11}$C, $^{13}$N and $^{15}$O, $^{75}$Br, $^{76}$Br and $^{124}$I. SPECT can use imaging agents labeled with, for example, the single-photon-emitters such as $^{201}$Tl, $^{99}$Tc, $^{123}$I, and $^{131}$I.

Glucose-based and amino acid-based compounds can be used as imaging agents. Amino acid-based compounds are more useful in analyzing tumor cells, due to their faster uptake and incorporation into protein synthesis. Of the amino acid-based compounds, $^{11}$C- and $^{18}$F-containing compounds have been used with success. $^{11}$C-containing radiolabeled amino acids suitable for imaging include, for example, L-[1-$^{11}$C]leucine (Keen et al. J. Cereb. Blood Flow Metab. 1989 (9):429-45), L-[1-$^{11}$C]tyrosine (Wiesel et al. J. Nucl. Med. 1991 (32):2041-49), L-[methyl-$^{11}$C]methionine (Comar et al. Eur. J. Nucl. Med. 1976 (1):11-14) and L-[1-$^{11}$C]methionine (Bolster et al. Appl. Radiat. Isot. 1986 (37):1069-70).

PET involves the detection of gamma rays in the form of annihilation photons from short-lived positron emitting radioactive isotopes including, but not limited to, $^{18}$F with a half-life of approximately 110 minutes, $^{11}$C with a half-life of approximately 20 minutes, $^{3}$N with a half-life of approximately 10 minutes and $^{15}$O with a half-life of approximately 2 minutes, using the coincidence method. For PET imaging studies, compounds such as [$^{11}$C]meta-hydroxyephedrine (HED) and 2-[$^{18}$F]fluoro-2-deoxy-D-glucose (FDG) can be used. SPECT can use longer-lived isotopes including, but not limited to, $^{99}$mTc with a half-life of approximately 6 hours and $^{201}$Tl with a half-life of approximately 74 hours. Radio-iodinated meta-iodobenzylguanidine (MIBG) is a radiotracing agent that can be used in nuclear medicine imaging studies.

3. Therapeutic and Prophylactic Agents

The nucleic acid nanostructures can be modified by covalent or non-covalent association with a therapeutic agent, and/or a prophylactic agent, particularly protein- or nucleic acid-based therapeutic and/or prophylactic agents. For example, one or more therapeutic and/or prophylactic agents can be associated with the exterior of the nucleic acid nanostructure, packaged within the hole at the center of the "doughnut", packaged within the closed cavity within the tube of the continuous torus-like structure, or combinations thereof. The positioning could be determined according to the design of the nanostructure and location of the site of interaction with the therapeutic and/or prophylactic agent.

The disclosed nanostructures can be used to carry, present, and/or deliver any therapeutic and/or prophylactic agents since they represent a general mode and platform for aiding in delivery of agents to cells and tissues. Thus, any therapeutic agent can be used as cargo in the disclosed nanostructure compositions. Comprehensive lists of therapeutic agents and drugs can be found in a number of places, such as the Orange Book and other lists maintained by the U.S. Food and Drug Administration (information available at websites fda.gov/Drugs/InformationOnDrugs/ucm129662.htm and fda.gov/Drugs/InformationOnDrugs/ApprovedDrugs/default.htm) and similar lists maintained by other countries, and at clinicaltrials.gov/ (for drugs and therapeutic agents undergoing clinical trials).

Useful therapeutic agents can be, for example, a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *Ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed compositions and methods.

In some forms, the therapeutic agents can be one or more small molecule kinase inhibitors or phytochemicals or nucleic acid drugs such as deoxyribozymes, ribozymes, siRNA, shRNA, DNA, PNAs, RNA and DNA aptamers, or miRNAs, small molecules, antibodies, peptides, amino acids, lipids, polysaccharides, growth factors, cytokines, bioactive peptides, enzymes, and cytotoxic drugs.

In some forms, the cargo comprises therapeutic and/or prophylactic agents, such as biologic agent(s), which can be physically entrapped, encapsulated, and/or non-covalently associated with the nanostructures.

Suitable biologic agents include monoclonal antibodies (mAbs), polyclonal antibodies, immunoglobulin, and antigen binding fragments thereof, growth factors (e.g., recombinant human growth factors), antigens, interferons, cytokines, hormones, and other proteins, amino acids, and peptides such as insulin, and combinations thereof. In some instances, the biologic agents are monoclonal antibodies (mAb) selected from infliximab (REMICADE®), adalimumab (HUMIRA®), or combinations thereof.

Other antibodies known in the art include, but are not limited to, those discussed in Kaplon H et al., MAbs. 2018 Febuary/March; 10(2):183-203, which is specifically incorporated by reference in entirety. Exemplary antibodies include lanadelumab, crizanlizumab, ravulizumab, eptinezumab, risankizumab, satralizumab, brolucizumab, PRO140, sacituzumab govitecan, moxetumomab pasudotox, cemiplimab, ublituximab, lampalizumab, roledumab, emapalumab, fasinumab, tanezumab, etrolizumab, NEOD001, gantenerumab, anifrolumab, tremelimumab, isatuximab, BCD-100, carotuximab, camrelizumab, IBI308, glembatumumab vedotin, mirvetuximab soravtansine, oportuzumab monatox, L19IL2/L19TNF.

Other antibodies are disclosed in International Publication No. WO2017186928, WO2018007327, WO2018031954, WO2018039247, WO2018015539, and U.S. Patent Publication No. US20180037634, US20180000935, each of which is specifically incorporated by reference in entirety.

Exemplary biologic agents can also be FDA approved therapeutic monoclonal antibodies which include, but are not limited to, ACTEMRA® (tocilizumab, GENENTECH), ADCETRIS® (brentuximab vedotin, SEATTLE GENETICS), AMJEVITA® (adalimumab-atto, AMGEN INC), ANTHIM® (obiltoxaximab, ELUSYS THERAPEUTICS INC), ARZERRA® (ofatumumab, GLAXO GRP LTD), AVASTIN® (bevacizumab, GENENTECH), BAVENCIO® (avelumab, EMD SERONO INC), BENLYSTA® (belimumab, HUMAN GENOME SCIENCES INC.), BESPONSA® (inotuzumab ozogamicin, WYETH PHARMS INC), BLINCYTO® (blinatumomab, AMGEN), CAMPATH® (alemtuzumab, GENZYME), CIMZIA® (certolizumab pegol, UCB INC), CINQAIR® (reslizumab, TEVA RESPIRATORY LLC), COSENTYX® (secukinumab, NOVARTIS PHARMS CORP), CYLTEZO® (adalimumab-adbm, BOEHRINGER INGELHEIM), CYRAMZA® (ramucirumab, ELI LILLY AND CO), DARZALEX® (daratumumab, JANSSEN), DERMABET® (betamethasone valerate, TARO), DUPIXENT® (dupilumab, REGENERON PHARMACEUTICALS), EMPLICITI® (elotuzumab, BRISTOL MYERS SQUIBB), ENTYVIO® (vedolizumab, TAKEDA PHARMS USA), ERBITUX® (cetuximab, IMCLONE), FASENRA® (benralizumab, ASTRAZENECA AB), GAZYVA® (obinutuzumab, GENENTECH), HEMLIBRA® (emicizumab, GENENTECH INC), HERCEPTIN® (trastuzumab, GENENTECH), HUMIRA® (adalimumab, ABBVIE INC), ILARIS® (canakinumab, NOVARTIS PHARMS), ILUMYA® (tildrakizumab-asmn, MERCK SHARP DOHME), IMFINZI® (durvalumab, ASTRAZENECA UK LTD), INFLECTRA® (infliximab-dyyb, CELLTRION INC), IXIFI® (infliximab-qbtx, PFIZER INC), KADCYLA® (ado-trastuzumab emtansine, GENENTECH), KEVZARA® (sarilumab, SANOFI SYNTHELABO), KEYTRUDA® (pembrolizumab, MERCK SHARP DOHME), LARTRUVO® (olaratumab, ELI LILLY AND CO), LEMTRADA® (alemtuzumab, GENZYME), LUCENTIS® (ranibizumab, GENENTECH), MVASI® (bevacizumab-awwb, AMGEN INC), MYLOTARG® (gemtuzumab ozogamicin, WYETH PHARMS INC), MYOSCINT® (imciromab pentetate, CENTOCOR INC), NUCALA® (mepolizumab, GLAXOSMITHKLINE LLC), OCREVUS® (ocrelizumab, GENENTECH INC), OGIVRI® (trastuzumab-dkst, MYLAN GMBH), OPDIVO® (nivolumab, BRISTOL MYERS SQUIBB), PERJETA® (pertuzumab, GENENTECH), PORTRAZZA® (necitumumab, ELI LILLY CO), PRALUENT® (alirocumab, SANOFI AVENTIS), PRAXBIND® (idarucizumab, BOEHRINGER INGELHEIM), PROLIA® (denosumab, AMGEN), PROSTASCINT® (capromab pendetide, CYTOGEN), RAXIBACUMAB® (raxibacumab, HUMAN GENOME SCIENCES INC.), REMICADE® (infliximab, CENTOCOR INC), RENFLEXIS® (infliximab-abda, SAMSUNG BIOEPSIS CO LTD), REOPRO® (abciximab, CENTOCOR INC), REPATHA® (evolocumab, AMGEN INC), RITUXAN® (rituximab, GENENTECH), SILIQ® (brodalumab, VALEANT LUXEMBOURG), SIMPONI ARIA@ (golimumab, JANSSEN BIOTECH), SIMULECT® (basiliximab, NOVARTIS), SOLIRIS® (eculizumab, ALEXION PHARM), STELARA® (ustekinumab, CENTOCOR ORTHO BIOTECH INC), STELARA® (ustekinumab, JANSSEN BIOTECH), SYLVANT® (siltuximab, JANSSEN BIOTECH), SYNAGIS® (palivizumab, MEDIMMUNE), TALTZ® (ixekizumab, ELI LILLY AND CO), TECENTRIQ® (atezolizumab, GENENTECH INC), TREMFYA® (guselkumab, JANSSEN BIOTECH), TROGARZO® (ibalizumab-uiyk, TAIMED BIOLOGICS USA), TYSABRI® (natalizumab, BIOGEN IDEC), UNITUXIN® (dinutuximab, UNITED THERAP), VECTIBIX® (panitumumab, AMGEN), XGEVA® (denosumab, AMGEN), XOLAIR® (omalizumab, GENENTECH), YERVOY® (ipilimumab, BRISTOL MYERS SQUIBB), ZEVALIN® (ibritumomab tiuxetan, SPECTRUM PHARMS), ZINBRYTA® (daclizumab, BIOGEN), ZINPLAVA® (bezlotoxumab, MERCK SHARP DOHME).

Other types of therapeutic or prophylactic agents can be selected from proteins, anti-inflammatory drugs, non-anti-inflammatory agents, steroids, anesthetics (such as lidocaine), analgesics, anti-pyretic agents, anti-infectious agents such as antibacterial, antifungal agents, contraceptives, immunosuppressants, chemotherapeutics, growth factors, cytokines, immunomodulatory molecules. These can be small molecules, proteins, peptides, sugars and polysaccharides, lipids and lipoproteins or lipopolysaccharides, and nucleic acids such as small interfering RNA, microRNA, PiRNA, ribozymes, and nucleotides encoding proteins or peptides. In some cases, cells can be cargo (e.g., therapeutic and/or prophylactic agent).

4. Other Agents/Cargo

In some forms, the nucleic acid nanostructures include gene editing moieties, or to include components capable of binding to gene editing moieties. Exemplary gene-editing moieties that can be included as cargo are CRISPR RNAs, for the gene editing through the CRISPR/Cas system, zinc finger nucleases, talens, and triplex forming oligonucleotides.

CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, Science, 15:339(6121):819-823 (2013) and Jinek, et al., Science, 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/

176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some forms, the nanostructures can carry, present, and/or deliver a CRISPR ribonucleoprotein complex (e.g., Cas9 protein+gRNA), an RNA guided endonuclease (or mRNA encoding such), a crRNA, a guide RNA, a tracr RNA, or combinations thereof.

In some forms, the nucleic acid nanostructures include zinc finger nuclease protein or a nucleic acid construct or constructs encoding a zinc finger nuclease (ZFN). ZFNs are typically fusion proteins that include a DNA-binding domain derived from a zinc-finger protein linked to a cleavage domain.

The most common cleavage domain is the Type IIS enzyme Fok1. Fok1 catalyzes double-stranded cleavage of DNA, at 9 nucleotides from its recognition site on one strand and 13 nucleotides from its recognition site on the other. See, for example, U.S. Pat. Nos. 5,356,802, 5,436,150, 5,487, 994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31, 978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

In some forms, DNA, RNA, PNA, protein, peptide, lipid, carbohydrate, a small-molecule, or a dye, or combinations thereof is contained as cargo in the described nanostructures.

In some forms, the cargo comprises a functional nucleic acid (e.g., antisense nucleic acid, mRNA, miRNA, piRNA, siRNA or combination thereof). Functional nucleic acids that inhibit the transcription, translation or function of a target gene are described.

Functional nucleic acids are nucleic acid molecules that have a specific function, such as binding a target molecule or catalyzing a specific reaction. Functional nucleic acid molecules can be divided into the following non-limiting categories: antisense molecules, RNAi (siRNA, miRNA, and piRNA), aptamers, ribozymes, triplex forming molecules, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

In some forms, the functional nucleic acid is siRNA, shRNA, miRNA, or piRNA. In some forms, the composition includes a vector expressing the functional nucleic acid. Methods of making and using vectors for in vivo expression of functional nucleic acids such as antisense oligonucleotides, siRNA, shRNA, miRNA, piRNA, EGSs, ribozymes, and aptamers are known in the art.

Prior work has shown that DNA origami as a carrier for anti-cancer drugs such as doxorubicin had increased cellular internalization and increased target cell killing as well as circumvented drug resistance (Jiang Q et al., *Journal of the American Chemical Society* 134.32: 13396-13403 (2012)). Therefore, in some forms, small molecules, such the anti-cancer drug doxorubicin, can be incorporated into the nanostructures through intercalation.

In some forms, a cargo can comprise a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a *vinca* alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab; paclitaxel such as Abraxane; Doxil.

In some forms, a cargo can comprise a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic peptides; immunomodulatory peptides, pro-inflammatory peptides, immunostimulating peptides; anti-inflammatory peptides; immunosuppressing peptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon-α. (IFN-α); interferon-γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain,

*Pseudomonas* exotoxin A, cholera toxin, a ligand fusion toxin such as DAB389EGF or ricin; a pro-apoptotic polypeptide, such as $_D$(KLAKLAK)$_2$ (SEQ ID NO:13); an immunomodulatory peptide; a pro-inflammatory peptide, an immunostimulating peptide; an anti-inflammatory peptide; an immunosuppressing peptide; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide."

In some forms, a cargo can comprise a pro-apototic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a pro-cell survival agent, a cell differentiating agent, a neuroprotective agent, an anti-arthritic agent, an anti-viral agent, a pro-apototic agent, an immunomodulatory agent, a pro-inflammatory agent, an immunostimulating agent, an anti-inflammatory agent, an immunosuppressing agent, an anti-angiogenic agent, a pro-angiogenic agent, a toxin, an a cytotoxic agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a chemotherapeutic agent, a contrast agent, an imaging agent, a label, a labeling agent, or a combination thereof.

D. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits comprising one or more compositions of nucleic acid nanostructures and instructions for use. The kits also can contain articles of manufacture such as structures, machines, devices, and the like, and compositions, compounds, materials, and the like for use with the provided nanostructure containing compositions.

Methods

The disclosed methods and compositions are suitable for several applications, including but not limited to, therapeutic, diagnostic, and analytical applications. Also provided herein are nanostructures useful for the transport and administration of therapeutic agents, bioactive compounds, biomolecular reagents, biocatalysts, and other molecular compounds of interest, referred to generally herein as cargo. Other uses are disclosed, apparent from the disclosure, and/or will be understood by those in the art.

Described herein are various methods related to the disclosed nucleic acid nanostructures and their use. For example, disclosed are methods of assembly of nucleic acid nanostructures, production of nucleic acid nanostructures, attachment and/or encapsulation of cargo to the nucleic acid nanostructures, and administration of nucleic acid assembly compositions for various applications.

In particular, disclosed are methods of delivery of a therapeutic, toxic, imaging, diagnostic, or prophylactic agent to a subject by administering to the subject any of the nanostructures provided herein.

Also provided are methods of treating a disease or disorder in a subject. The method of treatment can include administering to the subject a disclosed nucleic acid nanostructure that delivers an effective amount of a therapeutic and/or prophylactic agent to one or more targeted cells or tissues in the subject.

Also disclosed are any of the disclosed nanostructure compositions for use in the detection and/or diagnosis of a specific state or condition in a subject, e.g., cancer. Also disclosed are any of the disclosed compositions for use in the visualization of cancer in a subject. Also disclosed are any of the disclosed compositions for use in the localization of cancer in a subject.

Also disclosed is use of any of the disclosed compositions for the manufacture of a medicament for cancer treatment. Also disclosed is use of any of the disclosed compositions for the manufacture of a medicament for cancer detection.

Also disclosed are cancer diagnosis methods comprising administering an effective amount of any one or more of the disclosed compositions to a subject in need thereof.

A. Administration of Nucleic Acid Assembly Compositions

The disclosed nucleic acid nanostructure compositions can be administered to any cell, tissue, or subject in need thereof. Generally, the nucleic acid nanostructure compositions can be administered to cells, tissues, and subjects based on the cargo of the nucleic acid nanostructure and the need for the cargo of the cells, tissues, and subjects.

It is contemplated that the disclosed compositions can be administered by any method sufficient to deliver an effective amount of the nanostructure, including intravenous injection. The compositions for use in the disclosed methods include compositions where the nanostructures, and cargo contained therein, are contained in an amount effective to achieve the intended purpose.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject (e.g., a mammal, such as a human). A "cell" can be a cell from any organism including, but not limited to, a bacterium.

In some forms, the compositions described herein can be administered to a subject comprising a human or an animal including, but not limited to, a mouse, dog, cat, horse, bovine or ovine and the like, that is in need of alleviation or amelioration from a recognized medical condition.

By the term "effective amount" of a composition (e.g., nanostructure containing composition) as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

In some forms, the dosage of the disclosed compounds and compositions introduced or administered to a subject is an amount effective to provide a desired therapeutic, toxic, imaging, diagnostic, and/or prophylactic effect. For example, in some forms, the amount of the nanostructures and compositions thereof administered, is an amount effective to image or visualize a tissue, organ or region in a subject. In some forms, the amount of the nanostructures and compositions thereof administered, is an amount effective to diagnose a subject as having a particular disease, disorder, injury, abnormality, or defect, etc., such as a tumor or cancer. In some forms, the amount of the nanostructures and compositions thereof administered, is an amount effective to provide a toxic effect to cells, tissues, or regions in a subject. In some forms, the amount of the nanostructures and compositions thereof administered, is an amount effective to treat or prevent one or more diseases or disorders, or symptoms thereof, in a subject. For example, in some forms, the amount of the nanostructures and compositions thereof administered, is an amount effective to reduce tumor burden, to reduce tumor growth, to reduce cancer cell proliferation or viability, or combinations thereof, in a subject.

The efficacy of administration of a particular dose of the compositions according to the methods described herein can be determined by evaluating the particular forms of the medical history, signs, symptoms, and objective laboratory tests that are known to be useful in evaluating the status of a subject in need treatment of a given diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

Any of the disclosed compositions can be used in combination with a pharmaceutically acceptable carrier. The compositions (e.g., nanostructure containing compositions) described herein can be conveniently formulated into pharmaceutical compositions composed of one or more of the compositions in association with a pharmaceutically acceptable carrier. See, e.g., Remington's Pharmaceutical Sciences, latest edition, by E. W. Martin Mack Pub. Co., Easton, PA, which discloses typical carriers and conventional methods of preparing pharmaceutical compositions that can be used in conjunction with the preparation of formulations of the compositions described herein and which is incorporated by reference herein. These most typically would be standard carriers for administration of compositions to humans. In some forms, these include solutions such as sterile water, saline, and buffered solutions at physiological pH. Other compositions will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

The nanostructures and pharmaceutical compositions thereof described herein can be administered to the subject in a number of ways depending on whether local or systemic treatment is desired, and on the area to be treated. Any suitable route of administration can be used for the disclosed nanostructures and pharmaceutical compositions. Routes of administration can, for example, include topical, enteral, local, systemic, or parenteral. For example, administration can be intratumoral, peritumoral, epicutaneous, inhalational, enema, conjunctival, eye drops, ear drops, alveolar, nasal, intranasal, vaginal, intravaginal, transvaginal, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

Thus, for example, a pharmaceutical composition described herein can be administered as an ophthalmic solution and/or ointment to the surface of the eye. Moreover, a pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

The disclosed compositions and methods can be further understood through the following numbered paragraphs.

1. A nucleic acid nanostructure having a continuous torus-like structure with a closed three-dimensional cavity, the nanostructure comprising a plurality of subunits, wherein each of the subunits comprises a core domain and a connecting domain, wherein the core domain defines a polygon having a plurality of edges that enclose an open area, wherein the edges and open area define a plane of the subunit, wherein the connecting domain comprises one or more linkers, wherein a first edge of each subunit is coplanar with the first edges of the other subunits, wherein each of the subunits is between and connected to two other of the subunits with the planes of the connected subunits facing each other thereby forming a stack of subunits, wherein the planes of the connected subunits are substantially perpendicular to the plane of the first edges of the subunits and are tilted relative to the subunits connected to a given subunit in the direction horizontal to the plane of the first edges of the subunits, wherein the tilt between the planes of connected subunits produces a curve in the stack of subunits whereby the connected subunits form the continuous torus-like structure with a closed three-dimensional cavity defined by the open areas of the stacked subunits, wherein the connection between the subunits is made by the linkers, wherein each linker has a length, wherein the length of each linker is configured to create the tilt between the planes of connected subunits and thereby produce the continuous torus-like structure, wherein the subunits and linkers in the nanostructure form an extended supramolecular corkscrew.

2. The nanostructure of paragraph 1, wherein the polygon of each of the subunits is a hexagon, an octagon, a pentagon, a heptagon, a quadrilateral, or a triangle.

3. The nanostructure of paragraph 1 or 2 having an internal diameter, an external diameter, or both, of 50-100 nm, inclusive.

4. The nanostructure of any one of paragraphs 1-3 comprising 8-40 subunits, inclusive.

5. The nanostructure of paragraph 4 comprising 16 or 32 subunits.

6. The nanostructure of any one of paragraphs 1-5, wherein each subunit comprises 6-20 single-stranded nucleic acid strands.

7. The nanostructure of paragraph 6, wherein each subunit comprises 12 single nucleic acid strands.

8. The nanostructure of any one of paragraphs 1-7, wherein the core domain comprises one scaffold nucleic acid strand and n−1 staple nucleic acid strands, wherein n is the number of sides in the polygons of the subunits, wherein each staple strand comprises a central region flanked by a 3' overhang region, a 5' overhang region, or both, wherein the central region of each staple strand binds to the scaffold strand to form a duplex region.

9. The nanostructure of paragraph 8, wherein the central region is flanked by both the 3' overhang region and the 5' overhang region.

10. The nanostructure of any one of paragraphs 1-9, wherein the polygon of each of the subunits is a hexagon or an octagon.

11. The nanostructure of paragraph 10, wherein the polygon of each of the subunits is a hexagon.

12. The nanostructure of paragraph 11, wherein the core domain comprises one scaffold nucleic acid strand (strand 1) and five staple nucleic acid strands (strands 2-6), wherein each staple strand comprises a central region flanked by a 3' overhang region, a 5' overhang region, or both, wherein the central region of each staple strand binds to the scaffold strand to form a duplex region.

13. The nanostructure of paragraph 12, wherein the central region is flanked by both the 3' overhang region and the 5' overhang region.

14. The nanostructure of any one of paragraphs 8-13, wherein each pair of duplex regions adjacent to each other is configured to form a dihedral angle, wherein each of the dihedral angles is approximately the angle of a vertex of the polygon.

15. The nanostructure of paragraph 14, wherein the dihedral angle is 120°.

16. The nanostructure of any one of paragraphs 8-15, wherein each overhang is at about a 900 dihedral angle to the flanking duplex region.

17. The nanostructure of any one of paragraphs 8-16, wherein the 5' overhangs each individually comprise 8-16 nucleotides, inclusive, the 3' overhangs each individually comprise 8-16 nucleotides, inclusive, or both.

18. The nanostructure of any one of paragraphs 8-17, wherein each duplex region of the subunit comprises 20 base pairs, and wherein a thymidine residue is present between each duplex region.

19. The nanostructure of any one of paragraphs 8-18, wherein an unpaired thymidine residue is present on each strand of the core domain between the central region and one or both of the overhang regions.

20. The nanostructure of any one of paragraphs 8-19, wherein the connecting domain comprises n single-stranded nucleic acid linkers, wherein the linkers are complementary to one or more overhang regions of the core domain.

21. The nanostructure of any one of paragraphs 8-19, wherein the connecting domain comprises six single-stranded nucleic acid linkers (strands 7-12), wherein the nucleic acid linkers are complementary to one or more overhang regions of the core domain.

22. The nanostructure of any on of paragraphs 19-21, wherein the degree of complementarity between one or more linkers of the connecting domain and overhang regions of the core domain is in the range of 16-32 base pairs, inclusive.

23. The nanostructure of any one of paragraphs 1-22, wherein the nucleic acid, nucleic acid strands, and linkers are DNA.

24. The nanostructure of any one of paragraphs 6-23, wherein all of the strands and linkers are unique in sequence.

25. The nanostructure of any one of paragraphs 1-24 further comprising a therapeutic, toxic, targeting, imaging, diagnostic or prophylactic agent, or combinations thereof.

26. The nanostructure of any one of paragraphs 1-24 further comprising an imaging agent, wherein the imaging agent comprises a gold nanoparticle.

27. The nanostructure of any one of paragraphs 1-24 further comprising a targeting agent, wherein the targeting agent comprises an aptamer.

28. The nanostructure of any one of paragraphs 1-24 further comprising a molecule, wherein the molecule is DNA, RNA, PNA, protein, peptide, lipid, carbohydrate, a small-molecule, or a dye.

29. The nanostructure of any one of paragraphs 25-28, wherein the agent or molecule is covalently or non-covalently bound to the nanostructure.

30. The nanostructure of any one of paragraphs 25-28, wherein the agent or molecule is encapsulated within the nanostructure.

31. A method of delivery of a therapeutic, toxic, imaging, diagnostic, or prophylactic agent to a subject, the method comprising administering the nanostructure of any one of paragraphs 25-30 to the subject.

32. A method of making the nanostructure of any one of paragraphs 1-24, the method comprising applying a temperature transition to a mixture comprising the strands and the linkers such that the strands and linkers anneal.

33. The method of paragraph 32, wherein the temperature transition occurs over 16 hours.

34. The method of paragraph 32 or 33, wherein the temperature transition comprises a change in temperature from 90° C. to 20° C.

35. The method of any one of paragraphs 32-34, wherein the strands and linkers are present at approximately equal molar concentrations.

The present invention will be further understood by reference to the following non-limiting examples.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

Example 1: Formation of DNA Mazzocchio Nanostructure Using Single-Stranded DNA Oligonucleotides Methods ssDNA Design Twelve single-stranded DNA sequences to prepare a DNA mazzocchio composed of hexagonal subunits were designed using Tiamat (Williams S., et al., In *DNA Computing. DNA 2008. Lecture Notes in Computer Science*, Vol. 5347 (eds Goel, A. Simmel, F. C. & Sosik, P.) pp 90-101 (2008)). Six single-stranded DNA oligonucleotides were used to fabricate the core hexagon subunit and six other linking strands of different lengths were used to connect the subunits and induce curvature at the same time (FIGS. 1B-1C).

The single-stranded DNA oligonucleotides were obtained by solid-phase synthesis and purified by standard desalting. The sequences are provided below:

```
Strand 1:
                                      (SEQ ID NO: 1)
GATAGGCCGAGATCTGAGGATGCTGGCTCACGCCATTGGCTCGCGAC
CCCGTCCGCTAGACGTTATGCACAAGGCGTTGTCATTAGATGCTTAG
GTGCTCAGGCCGTAATGAGGCCGCTTGGCTGCGTTCCTCCGCCGCTT
GGGAACAGCCCCGC Strand 2:
                                      (SEQ ID NO: 2)
TCCAGCTCTGCGGACGGGGTCGCGAGCCATTCGAGGGCT Strand 3:
                                      (SEQ ID NO: 3)
TCGCCTGTAATACGCCTTGTGCATAACGTCTTGCCAACCC Strand 4:
                                      (SEQ ID NO: 4)
TGCCCGTACCCTGGTGCACCTAAGCATCTAATGACTCTGCGGAAGA Strand 5:
                                      (SEQ ID NO: 5)
TACCCCACTTTAGCGATAGCGGCCTCATTACGGCCTGTGCTACCCGT
ACGGA Strand 6:
                                      (SEQ ID NO: 6)
ATCAGTACGATTGGCGTGAGCCAGCATCCTCTAGCGGCGGAGGAACG
CAGCCTAGGCGGAACTCTTCGG Strand 7:
                                      (SEQ ID NO: 7)
TCGCTAAAGTGGGGTACCGAAGAGTTCCGCCT Strand 8:
                                      (SEQ ID NO: 8)
GATCTCGGCCTATCGCGGGGCTGTTCCC Strand 9:
                                      (SEQ ID NO: 9)
TCGTACTGATGAGCCCTCGA
```

47

-continued

Strand 10:

(SEQ ID NO: 10)

GAGCTGGAGGGTTGGC

Strand 11:

(SEQ ID NO: 11)

TTACAGGCGATCTTCCGCAG

Strand 12:

(SEQ ID NO: 12)

CCAGGGTACGGGCATCCGTACGGGTAGC

In the above strand 1-12 sequences (SEQ ID NOs: 1-12), the bold-italic T nucleotides are turning points.

Formation of Nanostructure

The twelve single-stranded DNA sequences were assembled together through a thermal annealing process. Briefly, the single-stranded DNAs were first diluted as stock of 100 μM in nuclease free water. A solution containing equal amounts of the 12 single-stranded DNA oligonucleotides was prepared by mixing equal amounts of each oligonucleotide in 20 mM Tris, 2 mM EDTA and 12.5 mM magnesium acetate for a final concentration of 7.5 μM for each strand. Since this design of mazzocchio used 16 subunits, the concentration of mazzocchio prepared with this protocol was 468.75 nM. The mixture was then subjected to a slow annealing process in a thermal cycler. The temperature transition applied to the mixture was as follows: incubation at 90° C. for 5 minutes, followed by slow cooling from 90° C. to 20° C. at a rate of –0.1° C. per minute.

Gel Electrophoresis

Native polyacrylamide gel electrophoresis (PAGE) and agarose gel electrophoresis were used to verify the correct assembly of the single-stranded sequences into the mazzocchio. 150 nM of different combinations of DNA were ran into 12% polyacrylamide gel at 100 V and 4° C. for 1 hour. For visualization, the gel was stained with SyBr gold nucleic acid gel stain.

Transmission Electron Microscopy (TEM)

TEM was used to characterize the final DNA mazzocchio nanostructure. 5 μl of DNA mazzocchio samples were first adsorbed onto glow-discharged 400 mesh copper grids (Ted Pella, Inc.) for 1 minute. This was followed by staining with 2% uranyl acetate for 1 minute. The stained samples were washed twice by distilled water to remove excess uranyl acetate. Stained DNA mazzocchio samples on the grid were visualized using a Philips CM 100 Transmission Electron Microscope with 100 kV operating voltage. Electron photomicrographs of DNA mazzocchio were captured with magnification from 73,000×-105,000× on different positions of the grid. To experimentally determine the diameter of the DNA mazzocchio, images were analyzed by the ImageJ software.

Results

DNA mazzocchio is a nanostructure inspired by Da Vinci's 15th century investigations of geometry as a toroidal ring consisting of 32 sections of octagonal subunits (FIG. 1A). In this experiment, a DNA mazzocchio nanostructure composed of 16 hexagonal subunits (FIG. 1B); each composed of 12 single-stranded DNA oligonucleotides was successfully prepared (FIG. 1C). The twelve single-stranded DNA sequences were assembled together through a thermal annealing process and interact with each other as in FIG. 1C.

Characterization of the nanostructure via PAGE showed that the strands were assembled correctly. The sizes of the structures formed by various combinations of scaffold, staple, and linker DNA strands corresponded to the size expected for interaction of single strands. The size of final product mazzocchio was too large to be analyzed by PAGE, so further characterization was performed using agarose gel electrophoresis. The results demonstrated that the mazzocchio was of a finite size. This indicated that the introduction of curvature using linkers of various lengths was successful.

Using transmission electron microscopy (TEM), the average diameter of the mazzocchio nanostructures was found to be 49.30±10.37 nm (average of 60.48 nm, 47.43 nm, and 40 nm). This experimentally determined diameter corresponded to the designed/expected dimension.

Example 2: DNA Mazzocchio Nanostructures are More Effective at Carrying Doxorubicin than DNA Tetrahedron Nanostructures Methods The DNA mazzocchio (from Example 1) and DNA tetrahedron nanostructures were made through an annealing process. The multiple single-stranded DNAs were mixed in equal ratio and placed in a thermal cycler to heat up (95° C. for 5 minutes) followed by slow cooling (overnight down to 20° C.).

10 μM of doxorubicin was incubated with various concentrations of the DNA mazzocchio and DNA tetrahedron nanostructures (as shown on the X-axis of FIG. 2) for 1 hour at room temperature. Then, 13 μl of mixture was placed in a 384-well microtiter plate and inserted in the plate reader. The fluorescence was measured using a plate reader (Varioskan Flash by Thermo Fisher Scientific) at the following parameters: Excitation 488 nm/Emission 595 nm; bandwidth 12 nm; measurement time: 500 ms. Error bars were obtained as standard error from triplicate experiments.

Results

Figure 2:
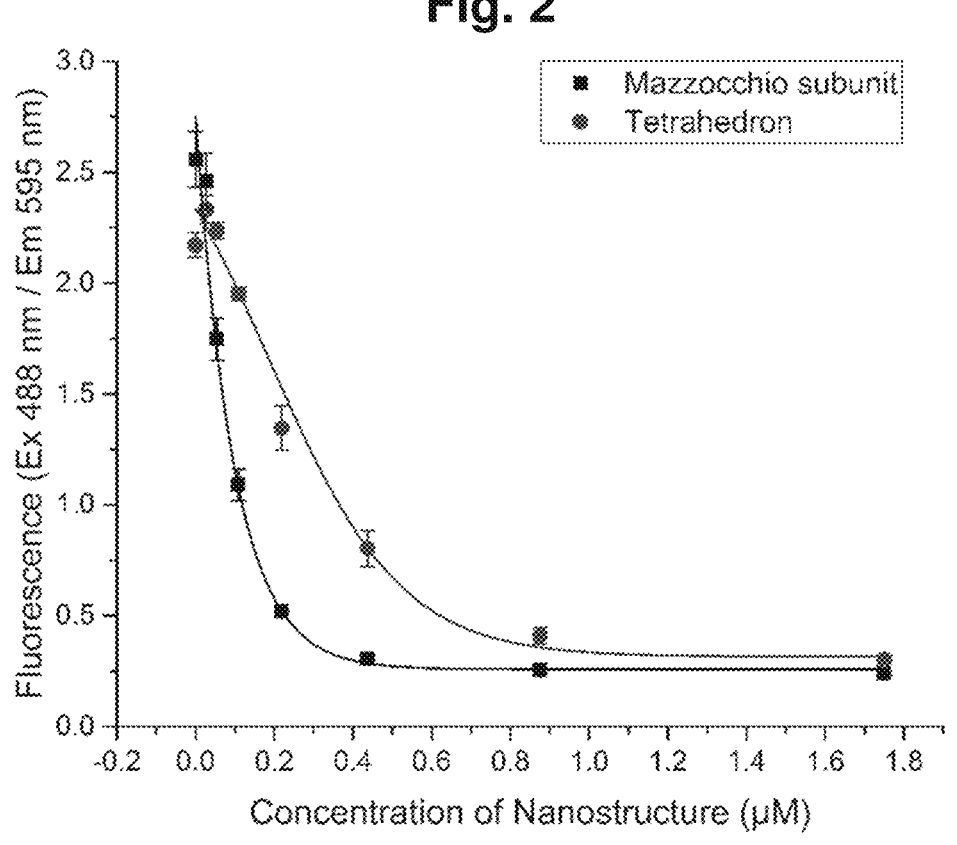
FIG. 2 is a graph showing the quantification of doxorubicin fluorescence from DNA tetrahedron and DNA mazzocchio nanostructures as a function of nanostructure concentration.

A DNA tetrahedron was used to compare with the DNA mazzocchio in terms of drug loading efficiency. The most commonly known anti-cancer drug is doxorubicin with the capability to intercalate into DNA and inhibit growth of cancer cell. Encapsulation with DNA nanostructures could protect normal cells from doxorubicin toxicity. It is important to develop effective carriers to deliver sufficient amounts of drug to cancer cells while maintaining the efficiency of getting into the cell. FIG. 2 shows the comparison between tetrahedron and mazzocchio for doxorubicin loading/encapsulation.

Since the intercalation of doxorubicin inhibited its fluorescence, the loading efficiency could be determined by the half maximal inhibitory concentration ($IC_{50}$). The $IC_{50}$ of tetrahedron and mazzocchio were found to be 1.54±0.36 μM and 0.48±1.92 μM respectively. It was observed that the mazzocchio was three times more effective in carrying doxorubicin as compared to the tetrahedron.

It is understood that the disclosed method and compositions are not limited to the particular methodology, protocols, and reagents described as these can vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a nanostructure" includes a plurality of such nanostructure, reference to "the nanostructure" is a reference to one or more nanostructures and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Unless the context clearly indicates otherwise, use of the word "can" indicates an option or capability of the object or condition referred to. Generally, use of "can" in this way is meant to positively state the option or capability while also leaving open that the option or capability could be absent in other forms or embodiments of the object or condition referred to. Unless the context clearly indicates otherwise, use of the word "may" indicates an option or capability of the object or condition referred to. Generally, use of "may" in this way is meant to positively state the option or capability while also leaving open that the option or capability could be absent in other forms or embodiments of the object or condition referred to. Unless the context clearly indicates otherwise, use of "may" herein does not refer to an unknown or doubtful feature of an object or condition.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. can include numerous options and alternatives, this should not be construed as, and is not an admission that, such options and alternatives are equivalent to each other or, in particular, are obvious alternatives. Thus, for example, a list of different cargo molecules does not indicate that the listed cargo molecules are obvious one to the other, nor is it an admission of equivalence or obviousness.

Every composition disclosed herein is intended to be and should be considered to be specifically disclosed herein. Further, every subgroup that can be identified within this disclosure is intended to be and should be considered to be specifically disclosed herein. As a result, it is specifically contemplated that any composition, or subgroup of compositions can be either specifically included for or excluded from use or included in or excluded from a list of compositions.

Those skilled in the art will recognize, or be able to ascertain using no more than routine experimentation, many equivalents to the specific embodiments of the method and compositions described herein. Such equivalents are intended to be encompassed by the following claims.

---

We claim:

1. A nucleic acid nanostructure having a continuous torus-like structure with a closed three-dimensional cavity, the nanostructure comprising a plurality of subunits, wherein each of the subunits comprises a core domain and a connecting domain, wherein the core domain defines a polygon having a plurality of edges that enclose an open area, wherein the edges and open area define a plane of the subunit, wherein the connecting domain comprises one or more linker nucleic acid strands, wherein a first edge of each subunit is coplanar with the first edges of the other subunits, wherein each of the subunits is between and connected to two other of the subunits with the planes of the connected subunits facing each other thereby forming a stack of subunits, wherein the planes of the connected subunits are substantially perpendicular to the plane of the first edges of the subunits and are tilted relative to the subunits connected to a given subunit in the direction horizontal to the plane of the first edges of the subunits, wherein the tilt between the planes of connected subunits produces a curve in the stack of subunits whereby the connected subunits form the continuous torus-like structure with a closed three-dimensional cavity defined by the open areas of the stacked subunits, wherein the core domain of each subunit comprises a scaffold nucleic acid strand and staple nucleic acid strands, wherein the connection between the subunits is made by the linker nucleic acid strands, wherein each linker comprises a length, wherein the length is configured to create the tilt between the planes of connected subunits and thereby produce the continuous torus-like structure, wherein each subunit comprises 6-20 single-stranded nucleic acid strands, and wherein the subunits and linkers in the nanostructure form an extended supramolecular corkscrew.

2. The nanostructure of claim 1, wherein the polygon of each of the subunits is a hexagon, an octagon, a pentagon, a heptagon, a quadrilateral, or a triangle.

3. The nanostructure of claim 1 comprising an internal diameter, an external diameter, or both, wherein the internal diameter, or the external diameter, or both the internal and external diameter comprises between about 50-100 nm, inclusive.

4. The nanostructure of claim 1 comprising 8-40 subunits, inclusive.

5. The nanostructure of claim 1, wherein the core domain comprises one scaffold nucleic acid strand and n−1 staple nucleic acid strands, wherein n is the number of sides in the polygons of the subunits, wherein each staple strand comprises a central region flanked by a 3' overhang region, a 5' overhang region, or both, and wherein the central region of each staple strand binds to the scaffold strand to form a duplex region.

6. The nanostructure of claim 1, wherein the polygon of each of the subunits is a hexagon.

7. The nanostructure of claim 5, wherein each pair of duplex regions adjacent to each other is configured to form a dihedral angle, wherein each of the dihedral angles is approximately the angle of a vertex of the polygon.

8. The nanostructure of claim 5, wherein each overhang is at about a 90° dihedral angle to the flanking duplex region.

9. The nanostructure of claim 5, wherein the 5' overhangs each individually comprise 8-16 nucleotides, inclusive, and/or wherein the 3' overhangs each individually comprise 8-16 nucleotides, inclusive.

10. The nanostructure of claim 5, wherein each duplex region of the subunit comprises 20 base pairs, and wherein a thymidine residue is present between each duplex region.

11. The nanostructure of claim 5, wherein an unpaired thymidine residue is present on each strand of the core domain between the central region and one or both of the overhang regions.

12. The nanostructure of claim 5, wherein the connecting domain comprises n single-stranded nucleic acid linkers, wherein the linkers are complementary to one or more overhang regions of the core domain.

13. The nanostructure of claim 12, wherein complementarity between one or more linkers of the connecting domain and overhang regions of the core domain is in the range of 16-32 base pairs, inclusive.

14. The nanostructure of claim 1, wherein one or more of the nucleic acid, nucleic acid strands, and linkers comprises DNA.

15. The nanostructure of claim 1, wherein all of the strands and linkers are unique in sequence.

16. The nanostructure of claim 1 further comprising a therapeutic, toxic, targeting, imaging, diagnostic or prophylactic agent, or combinations thereof.

17. The nanostructure of claim 16, wherein the agent is covalently or non-covalently bound to the nanostructure, or wherein the agent is encapsulated within the nanostructure.

18. A method of delivery of a therapeutic, toxic, imaging, diagnostic, or prophylactic agent to a subject, the method comprising administering the nanostructure of claim 16 to the subject.

19. A method of making the nanostructure of claim 1, the method comprising applying a temperature transition to a mixture comprising the strands and the linkers such that the strands and linkers anneal, thereby forming said nanostructure.

* * * * *

SEQUENCE LISTING

<160> NUMBER OF SEQ ID NOS: 13

<210> SEQ ID NO 1
<211> LENGTH: 155
<212> TYPE: DNA
<213> ORGANISM: Artificial Sequence
<220> FEATURE:
<223> OTHER INFORMATION: Synthetic sequence - strand 1

<400> SEQUENCE: 1
gataggccga gatctgagga tgctggctca cgccattggc tcgcgacccc gtccgctaga      60
cgttatgcac aaggcgttgt cattagatgc ttaggtgctc aggccgtaat gaggccgctt     120

-continued

```
ggctgcgttc ctccgccgct tgggaacagc cccgc                                    155

<210> SEQ ID NO 2
<211> LENGTH: 39
<212> TYPE: DNA
<213> ORGANISM: Artificial Sequence
<220> FEATURE:
<223> OTHER INFORMATION: Synthetic sequence - strand 2

<400> SEQUENCE: 2
tccagctctg cggacggggt cgcgagccat tcgagggct                                 39

<210> SEQ ID NO 3
<211> LENGTH: 40
<212> TYPE: DNA
<213> ORGANISM: Artificial Sequence
<220> FEATURE:
<223> OTHER INFORMATION: Synthetic sequence - strand 3

<400> SEQUENCE: 3
tcgcctgtaa tacgccttgt gcataacgtc ttgccaaccc                                40

<210> SEQ ID NO 4
<211> LENGTH: 46
<212> TYPE: DNA
<213> ORGANISM: Artificial Sequence
<220> FEATURE:
<223> OTHER INFORMATION: Synthetic sequence - strand 4

<400> SEQUENCE: 4
tgcccgtacc ctggtgcacc taagcatcta atgactctgc ggaaga                         46

<210> SEQ ID NO 5
<211> LENGTH: 52
<212> TYPE: DNA
<213> ORGANISM: Artificial Sequence
<220> FEATURE:
<223> OTHER INFORMATION: Synthetic sequence - strand 5

<400> SEQUENCE: 5
taccccactt tagcgatagc ggcctcatta cggcctgtgc tacccgtacg ga                  52

<210> SEQ ID NO 6
<211> LENGTH: 69
<212> TYPE: DNA
<213> ORGANISM: Artificial Sequence
<220> FEATURE:
<223> OTHER INFORMATION: Synthetic sequence - strand 6

<400> SEQUENCE: 6
atcagtacga ttggcgtgag ccagcatcct ctagcggcgg aggaacgcag cctaggcgga          60
actcttcgg                                                                  69

<210> SEQ ID NO 7
<211> LENGTH: 32
<212> TYPE: DNA
<213> ORGANISM: Artificial Sequence
<220> FEATURE:
<223> OTHER INFORMATION: Synthetic sequence - strand 7

<400> SEQUENCE: 7
tcgctaaagt ggggtaccga agagttccgc ct                                        32

<210> SEQ ID NO 8
```

```
<211> LENGTH: 28
<212> TYPE: DNA
<213> ORGANISM: Artificial Sequence
<220> FEATURE:
<223> OTHER INFORMATION: Synthetic sequence - strand 8

<400> SEQUENCE: 8
gatctcggcc tatcgcgggg ctgttccc                                          28

<210> SEQ ID NO 9
<211> LENGTH: 20
<212> TYPE: DNA
<213> ORGANISM: Artificial Sequence
<220> FEATURE:
<223> OTHER INFORMATION: Synthetic sequence - strand 9

<400> SEQUENCE: 9
tcgtactgat gagccctcga                                                   20

<210> SEQ ID NO 10
<211> LENGTH: 16
<212> TYPE: DNA
<213> ORGANISM: Artificial Sequence
<220> FEATURE:
<223> OTHER INFORMATION: Synthetic sequence - strand 10

<400> SEQUENCE: 10
gagctggagg gttggc                                                       16

<210> SEQ ID NO 11
<211> LENGTH: 20
<212> TYPE: DNA
<213> ORGANISM: Artificial Sequence
<220> FEATURE:
<223> OTHER INFORMATION: Synthetic sequence - strand 11

<400> SEQUENCE: 11
ttacaggcga tcttccgcag                                                   20

<210> SEQ ID NO 12
<211> LENGTH: 28
<212> TYPE: DNA
<213> ORGANISM: Artificial Sequence
<220> FEATURE:
<223> OTHER INFORMATION: Synthetic sequence - strand 12

<400> SEQUENCE: 12
ccagggtacg ggcatccgta cgggtagc                                          28

<210> SEQ ID NO 13
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(14)

<400> SEQUENCE: 13

Lys Leu Ala Lys Leu Ala Lys Lys Leu Ala Lys Leu Ala Lys
1               5                   10
```